US006852696B2

(12) United States Patent
Takashima et al.

(10) Patent No.: US 6,852,696 B2
(45) Date of Patent: Feb. 8, 2005

(54) INHIBITORS OF GLYCOSAMINOGLYCANS

(75) Inventors: Akira Takashima, Coppel, TX (US); Mark E. Mummert, Dallas, TX (US)

(73) Assignee: The University of Texas System, Austin, TX (US)

(*) Notice: Subject to any disclaimer, the term of this patent is extended or adjusted under 35 U.S.C. 154(b) by 0 days.

(21) Appl. No.: 10/105,774

(22) Filed: Mar. 20, 2002

(65) Prior Publication Data

US 2003/0054991 A1 Mar. 20, 2003

Related U.S. Application Data

(63) Continuation-in-part of application No. 09/532,709, filed on Mar. 22, 2000, now Pat. No. 6,653,285.
(60) Provisional application No. 60/126,475, filed on Mar. 26, 1999, and provisional application No. 60/277,790, filed on Mar. 21, 2001.

(51) Int. Cl.[7] .............................................. A61K 38/00
(52) U.S. Cl. ........................ 514/13; 530/326; 530/327; 530/300; 514/14; 514/2
(58) Field of Search ............................... 514/2, 13, 14, 514/11, 12; 530/326, 327, 324, 325

(56) References Cited

U.S. PATENT DOCUMENTS

2002/0042386 A1 * 4/2002 Rosen et al. .................. 514/44

FOREIGN PATENT DOCUMENTS

| EP | 0950708 A2 | 10/1999 |
| WO | WO 93/21312 A1 | 10/1993 |
| WO | WO 95/11924 | 5/1995 |
| WO | WO 97/09051 | 3/1997 |
| WO | WO 00/01841 | 1/2000 |
| WO | WO 00/68263 | 11/2000 |

OTHER PUBLICATIONS

Van Kuppelt et al., (1998), *J. Biol. Chem.*, 273(21):12960–12966.
Liang et al., (1997), *FEBS.*, 407:169–172.
Kubens et al., (1997), *Cancer Lett.*, 118:189–200.
Accession Number Smart 00445 at the NCBI Structure database, www.Ncbi.nlm.nih.gov.
Aruffo, et al. "CD44 is the principal cell surface receptor for hyaluronate", *Cell*, (1990) vol. 61: 1303–1313.
Barbas, et al. "Semisynthetic combinatorial antibody libraries: A chemical solution to the diversity problem." *Proc. Natl. Acad. Sci. USA*, (1992) vol. 89: 4457–4461.
Bartolazzi, et al. "Interaction between CD44 and hyaluronate is directly implicated in the regulation of tumor development", *J. Exp. Med.*, (1994) vol. 180: 53–66.
Bensouyad, et al. "Concentrations of glycosaminoglycans in synovial fluids and their relation with immunological and inflammatory mediators in rheumatoid arthritis", *Ann. Rheum. Dis.*, (1990) vol. 49: 301–307.
Bertrand, et al. "Hyaluronan (hyaluronic acid) and hyaluronectin in the extracellular matrix of human breast carcinomas; Comparison between invasive and non–invasive areas", *Int. J. Cancer.*, (1992) vol. 52: 1–6.
Camp, et al. "CD44 is necessary for optimal contact allergic responses but is not required for normal leukocyte extravasation", *J. Exp. Med.*, (1993) vol. 178: 497–507.
Culty, et al. "The hyaluronate receptor is a member or the CD44 (H–CAM) family of cell surface glycoproteins", *J. Cell. Biol.*, (1990) vol. 111: 2765.
Degrendele, et al. "CD44 and its Ligand hyaluronate mediate rolling under physiologic flow: A novel lymphocyte–endothelial cell primary adhesion pathway", *J. Exp. Med.*, (1996) vol. 183: 1119–1130.
Degrendele, et al. "CD44 activation and associated primary adhesion is inducible via T cell receptor stimulation", *J. Immunol.*, (1997) vol. 159: 2549–2553.
Degrendele, et al. "Requirement for CD44 in activated T cell extravasation into an inflammatory site", *Science*, (1997b) vol. 278: 672–675.
Delpech, et al. "Characterization and purification from human brain of a hyaluronic acid–binding glycoproteins, hyaluronectin", *J. Neurochem.* (1981) vol. 36: 855–859.
Dougherty, et al. "Ligand binding specificity of alternatively spliced CD44 isoforms–recognition and binding of hyaluronan by CD44R1", *The Journal of Biological Chemistry*, (1994) vol. 269(12): 9074–9078.
Garrard et al., "Selection of an anti–IGF–1 Fab from a Fab phage library created by mutagenesis of multiple CDR loops." *Gene*, (1993) vol. 128: 103–109.
Gmachl, et al. "The human sperm protein PH–20 has hyaluronidase activity", *F.E.B.S. Lett.*, (1993) vol. 336: 545–548.
Guo, et al. "Inhibition of human melanoma growth and metastasis in vivo by anti–CD44 monoclonal antibody", *Cancer Res.*, (1994) vol. 54:1561.
Hardingham, et al. "The role of link–protein in the structure of cartilage proteoglycan aggregates", *Biochem. J.*, (1979) vol. 177:237–247.

(List continued on next page.)

Primary Examiner—T. D. Wessendorf
(74) Attorney, Agent, or Firm—James S. Keddie; Bozicevic, Field & Francis LLP

(57) ABSTRACT

The present invention provides peptide derivatives with a specific affinity for glycosaminoglycan molecules. These peptide derivatives include multimers as well as chemically modified peptides and may be prepared by a variety of methods. The peptides of the invention have numerous functions, including but not limited to use as inhibitors of glycosaminoglycan-mediated signaling events and targeting agents. Peptides of the invention may be directed against any glycosaminoglycan, including hyaluronic acid, chondroitin sulfate A, chondroitin sulfate C, dermatan sulfate, heparin, keratan sulfate, keratosulfate, chitin, chitosan 1, and chitosan 2. The peptide derivatives of the invention also have therapeutic uses in the treatment and prevention of diseases involving inflammatory diseases, cancer, and cancer metastasis, autoimmune diseases, etc.

9 Claims, 11 Drawing Sheets

OTHER PUBLICATIONS

Hardwick, et al. "Molecular cloning of a novel hyaluronan receptor", *J. Cell. Biol.*, (1992) vol. 117: 1343–1350.

Horton, et al. "Hyaluronan fragments synergize with interferon–γ to induce the C–X–C chemokines mig and interferon–inducible protein–10 in mouse macrophage", *J. Biol. Chem.*, (1998) vol. 273: 35088–35094.

Horton, et al. "Regulation of hyaluronan–induced chemokines gene expression by IL–10 and IFN–γ in mouse macrophage", *J. Immunol.*, (1998) vol. 160: 3023–3030.

Itano, et al. "Molecular cloning of human hyaluron synthase", *Biochem. Biophys. Res. Commun.*, (1996) vol. 222: 816–820.

Kimata, et al. "Increased synthesis of hyaluronic acid by mouse mammary carcinoma cell variants with high metastatic potential", *Cancer. Res.*, (1983) vol. 43: 1347–1354.

Knudson, et al. "Hyaluronan–binding proteins in development, tissue homeostasis, and disease", *F.A.S.E.B. J.*, (1993) vol. 7: 1233–1241.

Knupfer, et al. "Hyaluronic acid binding capacity of malignant glioma cells", *Anticancer. Res.*, (1998) vol. 18: 353–356.

Laurent, et al. "Hyaluronan", *F.A.S.E.B. J.*, (1992) vol. 6: 2397–2404.

Le Baron, et al. "Hyaluronate binding properties of versican", *J. Biol. Chem.*, (1992) vol. 267: 10003–10010.

Lepperdinger, et al. "HYAL2, a human gene expressed in many cells, encodes a lysosomal hyaluronidase with a novel type of specificity", *J. Biol. Chem.*, (1998) vol. 273: 22466–22470.

Levesque, et al. "In vitro culture of human peripheral blood monocytes induces hyaluronan binding and up–regulates monocyte variant CD44 isoform expression", *The Journal of Immunology*, (1996) vol. 156: 1557–1565.

McKee, et al. "Hyaluronan (HA) fragments induce chemokines gene expression in alveolar macrophages", *J. Clin. Invest.*, (1996) vol. 98: 2403–2413.

Mikecz, et al. "Anti–CD44 treatment abrogates tissue oedema and leukocyte infiltration in murine arthritis", *Nat. Med.*, (1995) vol. 1: 558–563.

Miyake, et al. "Hyaluronate can function as a cell adhesion molecule and CD44 participates in hyaluronate recognition", *J. Exp. Med.*, (1990) vol. 172: 69–75.

Mohamadzadeh, et al. "Functional roles for granzymes in murine epidermal gamma (delta) T–cell–mediated killing of tumor targets", *J. Invest. Dermatol.*, (1996) vol. 107(5): 738–742.

Mummert, et al. "Development of a peptide inhibitor of hyaluronan–mediated leukocyte trafficking", *J. Exp. Med.*, (2000) vol. 192(6): 769–779.

Ozello, et al. "Growth–promoting activity of acid mucopolysaccharides on a strain of human mammary carcinoma cells", *Cancer. Res.*, (1960) vol. 20: 600–604.

Ranganathan, et al. "Hyaluronan mediates sperm motility by enhancing phosphorylation of proteins including hyaluronan binding protein", *Cell. Mol. Biol. Res.*, (1995) vol. 41: 467–476.

Rauch, et al. "Cloning and primary structure of neurocan, a developmentally regulated, aggregating chondroitin sulfate proteoglycan of brain", *J. Biol. Chem.*, (1992) vol. 267: 19536–19547.

Schubert, et al. "Collaborative interactions between growth factors and the extracellular matrix", *Trends Cell. Biol.*, (1992) vol. 2: 63–66.

Spelling, et al. "Glycosaminoglycans in the synovial fluids of patients with juvenile rheumatoid arthritis", *Clin. Exp. Rheumatol.*, (1991) vol. 9: 195–199.

Spicer, et al. "Molecular cloning and characterization of a putative mouse hyaluronan synthase", *J. Biol. Chem.*, (1996) vol. 271: 23400–23406.

Steinman. "The dendritic cell system and its role in immunogenicity", *Ann. Rev. Immunol.*, (1991) vol. 9: 271–296.

Takashima, et al. "New technologies to prevent and treat contact hypersensitivity responses", *Ann. N Y Acad. Sci.*, (2000) vol. 919: 205–213.

Takeucki, et al. "Variation in glycosaminoglycan components of breast tumors", *Cancer. Res.*, (1976) vol. 36: 2133–2139.

Turley, et al. "Hyaluronan and a cell–associated hyaluronan binding protein regulate the locomotion of ras–transformed Cells", *The Journal of Cell Biology*, (1991) vol. 112(5): 1041–1047.

Verdrengh, et al. "Administration of antibodies to hyaluronanreceptor (CD44) delays the start and ameliorates the severity of collagen II arthritis", *Scand. J. Immunol.*, (1995) vol. 42: 353–358.

Watanabe, et al. "Identification of Hyaluronan–binding Domains of Aggrecan", *J. Biol. Chem.*, (1997) vol. 272: 28057–28065.

\* cited by examiner

A

B

C

SEQUENCE LISTING

```
<160> NUMBER OF SEQ ID NOS: 18

<210> SEQ ID NO 1
<211> LENGTH: 12
<212> TYPE: PRT
<213> ORGANISM: Artificial Sequence
<220> FEATURE:
<223> OTHER INFORMATION: Synthetic polypeptide, wherein Xaa is any amino
      acid.
<220> FEATURE:
<221> NAME/KEY: VARIANT
<222> LOCATION: (3)...(3)
<223> OTHER INFORMATION: Xaa is any amino acid.
<220> FEATURE:
<221> NAME/KEY: VARIANT
<222> LOCATION: (7)...(7)
<223> OTHER INFORMATION: Xaa is any amino acid.

<400> SEQUENCE: 1

Gly Ala Xaa Trp Gln Phe Xaa Ala Leu Thr Val Xaa
  1               5                  10

<210> SEQ ID NO 2
<211> LENGTH: 12
<212> TYPE: PRT
<213> ORGANISM: Mus musculus

<400> SEQUENCE: 2

Gly Ala His Trp Gln Phe Asn Ala Leu Thr Val Arg
  1               5                  10

<210> SEQ ID NO 3
<211> LENGTH: 25
<212> TYPE: DNA
<213> ORGANISM: Mus musculus

<400> SEQUENCE: 3
tatccaaccg gccattcaat cactg                                            25

<210> SEQ ID NO 4
<211> LENGTH: 24
<212> TYPE: DNA
<213> ORGANISM: Mus musculus

<400> SEQUENCE: 4 atacccgct tgtcacacca cttg                                              24

<210> SEQ ID NO 5
<211> LENGTH: 24
<212> TYPE: DNA
<213> ORGANISM: Mus musculus

<400> SEQUENCE: 5
catcttcact ggccgaccct ttgt                                             24

<210> SEQ ID NO 6
<211> LENGTH: 22
<212> TYPE: DNA
<213> ORGANISM: Mus musculus
```

-continued

```
<400> SEQUENCE: 6
tcgccacccc agcccagata gc                                              22

<210> SEQ ID NO 7
<211> LENGTH: 19
<212> TYPE: DNA
<213> ORGANISM: Mus musculus

<400> SEQUENCE: 7
cctaggccta atgatggtg                                                  19

<210> SEQ ID NO 8
<211> LENGTH: 19
<212> TYPE: DNA
<213> ORGANISM: Mus musculus

<400> SEQUENCE: 8
gctagtatgg gctttgtgg                                                  19

<210> SEQ ID NO 9
<211> LENGTH: 23
<212> TYPE: DNA
<213> ORGANISM: Mus musculus

<400> SEQUENCE: 9
ctacgggcgc tgtcggtgaa ggt                                             23

<210> SEQ ID NO 10
<211> LENGTH: 24
<212> TYPE: DNA
<213> ORGANISM: Mus musculus

<400> SEQUENCE: 10
cggggacata gttagcagcc agtt                                            24

<210> SEQ ID NO 11
<211> LENGTH: 23
<212> TYPE: DNA
<213> ORGANISM: Mus musculus

<400> SEQUENCE: 11
tggaacaccg gaaaatgaag aag                                             23

<210> SEQ ID NO 12
<211> LENGTH: 23
<212> TYPE: DNA
<213> ORGANISM: Mus musculus

<400> SEQUENCE: 12
gaccgagccg tgtatttagt tgc                                             23

<210> SEQ ID NO 13
<211> LENGTH: 22
<212> TYPE: DNA
<213> ORGANISM: Mus musculus

<400> SEQUENCE: 13
ccatgaggcg ggtgaaggag ag                                              22

<210> SEQ ID NO 14
<211> LENGTH: 24
<212> TYPE: DNA
```

```
<213> ORGANISM: Mus musculus

<400> SEQUENCE: 14
atgcggccac ggtagaaaag ttgt                                              24

<210> SEQ ID NO 15
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 15

Gly Ala His Trp Gln Phe Asn Leu Ala Thr Val Arg Gly Gly Gly Ser
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 16

Arg Arg Gly Ala His Trp Gln Phe Asn Ala Leu Thr Val Arg Arg
 1               5                  10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 17

Arg Arg His Trp Gln Phe Asn Ala Leu Thr Val Arg Arg
 1               5                  10

<210> SEQ ID NO 18
<211> LENGTH: 16
<212> TYPE: PRT
<213> ORGANISM: Artificial Sequence
<220> FEATURE:
<223> OTHER INFORMATION: Synthetic polypeptide, wherein Xaa is any
      amino acid.
<220> FEATURE:
<221> NAME/KEY: VARIANT
<222> LOCATION: 3, 7, 12
<223> OTHER INFORMATION: Xaa is any amino acid

<400> SEQUENCE: 18

Gly Ala Xaa Trp Gln Phe Xaa Ala Leu Thr Val Xaa Gly Gly Gly Ser
 1               5                  10                  15
```

INHIBITORS OF GLYCOSAMINOGLYCANS

CROSS-REFERENCE TO RELATED APPLICATIONS

This application is a continuation-in-part application of U.S. patent application Ser. No. 09/532,709, now U.S. Pat. No. 6,653,285 entitled MODULATORS OF POLYSACCHARIDES AND USES THEREOF, filed Mar. 22, 2000 and claims priority to U.S. provisional Patent Application No. 60/277,790 entitled "INHIBITORS OF GLYCOSAMINOGLYCANS" filed Mar. 21, 2001 and 60/126,475, filed Mar. 26, 1999 the disclosures of these applications are hereby incorporated by reference in their entirety into this application for all purposes.

GOVERNMENT RIGHTS

The government may have certain rights in the present invention pursuant to grant number RO3 AR47402 from the National Institutes of Health.

FIELD OF THE INVENTION

The present invention relates generally to the fields of cancer, immunology and inflammatory diseases. More particularly, it concerns peptide inhibitors of glycosaminoglycans. The invention also provides therapeutic and preventive methods for the treatment of inflammatory diseases, autoimmune diseases and other glycosaminoglycan-associated diseases. Additionally, the invention provides anticancer therapies using glycosaminoglycan binding agents.

BACKGROUND OF THE INVENTION

Interactions of cells of the immune system with components of the extracellular matrix (ECM) are responsible for the induction of various immune responses including inflammatory responses. In addition to being an important component of the extracellular structure, the ECM also is involved in cellular signal transduction events by interactions with cellular receptors. Thus, the ECM modulates cell adhesion, cell proliferation, cell differentiation, etc. (Schubert et al. Trends Cell. Biol., 2:63–66, 1992). Major constituents of the ECM include glycosaminoglycans, fibronectin, laminin, collagens, and proteoglycans, which bind specific cell surface receptors via protein—protein and protein-carbohydrate interactions. The glycosaminoglycans are linear polymers of repeating disaccharides often bound covalently to a protein core.

Hyaluronan (also known as hyaluronic acid or hyaluronate) (HA), is a glycosaminoglycan lacking a protein core, and is one of the major non-structural elements of the extracellular matrix (Laurent et al., F.A.S.E.B. J. 6: 2397–2404, 1992; Aruffo et al. Cell. 61:1303–1313, 1990; Culty et al., J. Cell. Biol. 111:2765 1990; Underhill et al. Cell. Sci. 103, 293–298, 1992; Toole et al. Plenum Press, New York, 1384–1386,1991). HA also is expressed on cell surfaces and has been shown to bind several different molecules, including CD44 (Aruffo et al. Cell. 61:1303–1313, 1990; Miyake et al. J. Exp. Med. 172:69–75, 1990), the receptor for HA-mediated motility (RHAMM) (Hardwick et al. J. Cell. Biol 117:1343–1350, 1992), link protein (Hardingham et al. Biochem. J. 177:237–247, 1979), aggrecan (Watanabe et al. J. Biol. Chem. 272:28057–28065, 1997), versican (LeBaron et al. J. Biol. Chem. 267:10003–10010, 1992), hyaluronectin (Delpech et al. J. Neurochem. 36:855–859, 1981), neurocan (Rauch et al. J. Biol. Chem., 267:19536–19547, 1992), liver sinusoidal endothelial HA receptor, inter-α-trypsin inhibitor-related proteins (10), BEHAB (brain-enriched HA binding), CD38, lymphatic vessel endothelial HA receptor 1, and white fat/bone marrow/osteoblast HA binding proteins. Conversely, CD44 binds not only HA, but also collagens, fibronectin, chondroitin sulfates, heparin, heparin sulfate, and serglycins. Thus, although CD44 (or HA) is generally considered to be a primary HA receptor (or a principal CD44 ligand), HA-CD44 interaction represents one of the multiple mechanisms by which HA and CD44 may regulate cellular activities.

HA is a repeating disaccharide of $[GlcNAc\beta 1\text{-}4GlcUA\beta 1\text{-}3]_n$ that exists in vivo as a high molecular weight linear polysaccharide. HA is found in mammals predominantly in connective tissues, skin, cartilage, and in synovial fluid, and is also the main constituent of the vitreous of the eye. In connective tissue, the water of hydration associated with HA creates spaces between tissues, thus creating an environment conducive to cell movement and proliferation. HA plays a key role in biological phenomena associated with cell motility including rapid development, regeneration, repair, embryogenesis, embryological development, wound healing, angiogenesis, and tumorigenesis (Toole et al. Plenum Press, New York, 1384–1386,1991; Bertrand et al. Int. J. Cancer. 52:1–6, 1992; Knudson et al. F.A.S.E.B. J. 7:1233–1241, 1993). HA levels have been shown to correlate with tumor aggressiveness (Ozello et al. Cancer. Res. 20:600–604, 1960; Takeuchi et al. Cancer. Res. 36:2133–2139, 1976; Kimata et al. Cancer. Res. 43:1347–1354, 1983), and can be indicative of the invasive properties of tumor cells (Knupfer et al. Anticancer. Res. 18:353–6, 1998).

HA also is involved in immune responses, for example, increased binding of HA to one of its receptors, CD44, has been shown to mediate the primary adhesion ("rolling") of lymphocytes to vascular endothelial cells under conditions of physiologic shear stress, and this interaction mediates activated T cell extravasation into an inflamed site in vivo in mice (DeGrendele et al. J. Exp. Med. 183:1119–1130, 1996; DeGrendele et al., J. Immunol. 159:2549–2553, 1997; DeGrendele, et al., Science. 278:672–675, 1997b). Alterations in levels of HA and other glycosaminoglycans have also been associated with unwanted immune responses, and in diseases and disorders such as rheumatoid arthritis, atopic dermatitis, psoriasis, multiple sclerosis, transplantation rejection. For example, HA and other glycosaminoglycans display are altered in autoimmune disorders such as arthritis, and decreased levels of both hyaluronic acid and chondroitin 6-sulfate have been found in the diseased synovial fluid of both adults with rheumatoid arthritis (Bensouyad et al. Ann. Rheum. Dis. 49:301–307, 1990) and children with juvenile rheumatoid arthritis (Spelling et al. Clin. Exp.Rheumatol. 9:195–9, 1991).

Dendritic cells (DC) play essential roles in the induction of cellular immune responses to a variety of relevant antigens. DC are known to play critical roles in the induction of cellular immune responses against a wide variety of antigens of relevance, including chemical haptens, foreign proteins, infectious microbes, and tumor-associated antigens (Steinman et al. Ann. Rev. Immunol. 9:271, 1991; Stingl et al. ed. McGraw Hill and Co. New York, p. 172, 1993). Interaction between HA, expressed on endothelial cells, and CD44, expressed on activated dendritic cells as well as T cells, and granulocytes, is believed to mediate homing of such leukocytes to their target sites.

Glycosaminoglycans, particularly HA, also are known to mediate other cellular interactions that involve binding and entry into a cell. For example, HA is involved in infection of mammalian cells by the Human Immunodeficiency Virus (HIV), since HIV is known to bind to HA upon infection. Both HA and monoclonal antibodies to its receptor CD44 were found to inhibit HIV infection of monocytes by monocytotropic HIV (Levesque et al. *J. Immunol.* 156:1557–65, 1996). HA also is involved in mammalian zygote formation by mediating binding of the oocyte and the sperm. Data indicate that HA in the cumulus matrix may act to prime the fertilizing sperm for induction of the acrosome reaction by constituents of the cumulus and/or zona pellucida. HA is thought to mediate this interaction by binding to the PH-20 protein to increase basal levels of intracellular calcium and thereby potentiate the acrosome reaction (Sabeur et al. *Zygote*. 6:103–11, 1998). HA mediates sperm motility by enhancing phosphorylation of proteins including HA binding protein (Ranganathan et al. *Cell. Mol. Biol. Res.* 41:467–76, 1995).

Other important glycosaminoglycans involved in a variety of physiological and pathological states include, chondroitin sulfate A, chondroitin sulfate C, dermatan sulfate, heparin, keratan sulfate, keratosulfate, chitin, chitosan 1, and chitosan 2. These and other glycosaminoglycans, and particularly hyaluronic acid, play important roles in such varying physiological processes make them attractive targets for therapeutic agents. However, glycosaminoglyeans have been found to be nearly non-antigenic, and hence, very few antibodies that recognize glycosaminoglycans have been isolated. Due to the lack of antigenicity, it has been technically difficult to develop inhibitors or probes of glycosaminoglycans. As such, there is a need in the art for inhibitors of glycosaminoglycan-mediated processes, and in particular for inhibitors of hyaluronic acid-mediated processes.

SUMMARY OF THE INVENTION

Hyaluronic acid and salts play key roles in biological phenomena associated with cell motility including development, regeneration, repair, embryogenesis, embryological development, wound healing, angiogenesis, and tumorigenesis and immune responses. The present invention provides methods and compositions comprising artificial peptide multimers that have the ability to bind HA with a binding affinity $K_a$ of $5\times10^5$ l/mol or more and inhibit HA-dependent processes. In particular, several different aspects of the immune system, including inhibiting inflammatory reactions, inhibition of cytokine release, inhibition of antigen presentation, inhibition of clonal expansion of T-cells, inhibition of maturation of antigen-presenting cells (APCs) such as dendritic cells, inhibition of APC-T cell cluster formation, inhibition of T-cells activation and inhibition of cell adhesion, leucocyte extravasation, etc can be manipulated by the invention. The invention further provides therapeutic and preventive methods for the treatment of inflammatory diseases, autoimmune diseases and other glycosaminoglycan-associated diseases. Additionally, the invention provides anticancer therapies that inhibit tumorigensis and metastasis.

In a first embodiment, an artificial peptide multimer is disclosed which comprises the structure $(Z)_nX(Y)_m$ where X is any amino acid and each of Y and Z is an aliphatic or polar aliphatic amino acid of between 6 and 30 amino acid residues. The peptide multimer will bind a glycosaminoglycan or fragment thereof with a binding affinity $K_a$ of $5\times10^5$ l/mol or more. The structure $(Z)_nX(Y)_m$ is comprised within a subunit of the multimer. The multimer may have two or more peptide units with the same amino acid sequence, or with different amino acid sequences. The multimer may be a dimer, a trimer, a tetramer, a pentamer, a hexamer, a heptamer, an octamer, a nonamer, decamer or higher order multimer. The glycosaminoglycan bound may be hyaluronic acid or a salt thereof, chondroitin sulfate, chondroitin sulfate C, dermatan sulfate, heparin, keratan sulfate, keratosulfate, chitin, chitosan 1 or chitosan 2.

The multimer subunits may be connected by one or more linker molecules, such as amino acids (peptide linkers) or non-peptide linker (e.g., succinic acid, polyethylene glycol (PEG)). The peptide subunits may comprise a motif ZZZXZZZ, wherein Z is an amino acid selected from the group consisting of aliphatic and polar aliphatic residues, and wherein X is any amino acid. The subunit may further comprises an N- or C-terminal extension $W_p$, wherein W is any basic or neutral amino acid, and p is an integer between 3 and 13, for example, wherein W is arginine or glycine independently. The peptide subunit also may comprise a terminal serine. In a particular embodiment, the extension is a C-terminal GGGS.

In another embodiment, the peptide multimer may be chemically modified. The chemical modification comprises amidation, PEGylation, glycosylation, acetylation, prenylation, phosphorylation, biotinylation, carboxylation, carbonylation, or may be further derivatized by addition of known protecting/blocking groups (substitution with "bulky" side chains, e.g., methyl for alpha-hydroxyl). Other modifications include use of D-amino acids, cyclization, use of trans-olefin bonds. In particular embodiments, one or more of the peptide multimer subunits comprises the peptide sequence GAXWQFXALTVX (SEQ ID NO:1), wherein X is any amino acid. In a specific embodiment, the multimer comprises all GAHWQFNALTVR (SEQ ID NO:2) subunits. In a particular embodiment, the extension is a C-terminal GGGS.

In another embodiment, there is provided a pharmaceutical composition comprising (a) an artificial peptide multimer comprising the structure $(Z)_nX(Y)_m$ where X is any amino acid and each of Y and Z is an aliphatic or polar aliphatic amino acid of between 6 and 30 amino acid residues and having the ability to bind a glycosaminoglycan or fragment thereof with a binding affinity $K_a$ of $5\times10^5$ l/mol or more; and (b) a pharmaceutically acceptable carrier, diluent or excipient.

In a further embodiment, there is provided a method of inhibiting a glycosaminoglycan-mediated reaction comprising administering to a subject an agent that binds a glycosaminoglycan or fragment thereof with a binding affinity $K_a$ of $5\times10^5$ l/mol or more, preferably a $K_a$ of $1\times10^6$ l/mol or more, more preferably a $K_a$ of $1\times10^7$ l/mol or more, or even more preferably a $K_a$ of $1\times10^8$ l/mol or more, or $1\times10^9$ l/mol or more, or $1\times10^{10}$ l/mol or more, or $1\times10^{11}$ l/mol or more. The reaction may be an inflammatory reaction, such as the interaction of an antigen presenting cell such as a dendritic cell or macrophage and a T cell. The activity may comprise alteration in the secretion of immunoregulatory factors, cellular locomotion, cell-to-cell interaction, cell adhesion, cellular differentiation and maturation, cell growth and death, or inflammatory/immune reaction. Administration may be topical or systemic administration, or local or regional to an affected body part or organ. Additionally, the peptide may be chemically modified as discussed above.

In still yet a further embodiment, there is provided a method for treating or preventing cancer, tumorigenesis or cancer metastasis comprising administering to a subject in need thereof an agent having the ability to bind a glycosaminoglycan or fragment thereof with a binding affinity $K_a$ of $5 \times 10^5$ l/mol or more. The agent may be an artificial peptide multimer comprising the structure $(Z)_n X(Y)_m$ where X is any amino acid and each of Y and Z is an aliphatic or polar aliphatic amino acid of between 6 and 30 amino acid residues and having the ability to bind a glycosaminoglycan or fragment thereof with a binding affinity $K_a$ of $5 \times 10^5$ l/mol or more. The cancer may be brain cancer, lung cancer, throat cancer, esophageal cancer, cancer of the head and neck, skin cancer, breast cancer, stomach cancer, colon cancer, cancer of the rectum, cervical cancer, prostate cancer, ovarian cancer, liver cancer, pancreatic cancer or a cancer of the blood. The treatment may comprise inhibiting proximal or distal metastasis in a patient already suffering from cancer. The peptide may be administered local or regional to a solid tumor, or systemically. The peptide may be administered in conjunction with a second anti-cancer therapy, such as radiation, chemotherapy, or gene therapy. The second anti-cancer therapy may be administered concurrent, prior to or after the peptide. The glycosaminoglycan may be hyaluronic acid, chondroitin sulfate, chondroitin sulfate C, dermatan sulfate, heparin, keratan sulfate, keratosulfate, chitin, chitosan 1 or chitosan 2. The peptide may be a monomer or a multimer comprising two or more peptide subunits as discussed above. The peptide also may be chemically modified, also as discussed above. The peptide may comprise a motif ZZZXZZZ, wherein Z is an amino acid selected from the group consisting of aliphatic and polar aliphatic residues, and wherein X is any amino acid. In a specific embodiment, the peptide sequence may be GAXWQFXALTVX (SEQ ID NO:1), wherein X is any amino acid. In a particular embodiment, the extension is a C-terminal GGGS.

In another embodiment, there is provided a method of treating or preventing cancer comprising administering to a subject in need thereof a compound that modulates the synthesis, secretion or degradation of a glycosaminoglycan. The glycosaminoglycan may be hyaluronic acid, chondroitin sulfate, chondroitin sulfate C, dermatan sulfate, heparin, keratan sulfate, keratosulfate, chitin, chitosan 1 or chitosan 2. The treatment may comprise inhibiting metastasis in a patient already suffering from cancer. The peptide may be administered local or regional to a solid tumor, or administered systemically. The method also may comprise a second anti-cancer therapy.

In still another embodiment, there is provided a method of screening for an anti-cancer agent comprising (a) providing a cell that expresses a glycosaminoglycan; (b) contacting the cell with a candidate substance; and (c) measuring the synthesis, secretion, degradation, surface expression or function of the glycosaminoglycan, wherein a change in the synthesis, secretion, degradation, surface expression or function of a glycosaminoglycan, as compared to a similar cell not treated with the candidate substance, identifies the candidate substance as an anti-cancer agent.

In still yet another embodiment, there is provided a method of targeting an agent to a glycosaminoglycan structure comprising (a) providing a conjugate comprising a targeting moiety linked to the agent; and (b) contacting the conjugate with the cell. The targeting moiety may be covalently linked to the agent. The cell may be located in a subject, for example, a human subject. The glycosaminoglycan may be expressed on a cell or contained within extracellular matrix. The agent may be a therapeutic agent, such as a radionuclide or cancer chemotherapeutic, or a diagnostic agent. Also, it may be a hyaluronidase. The cell may be a cancer cell, and the glycosaminoglycan may be chondroitin sulfate, chondroitin sulfate C, dermatan sulfate, heparin, keratan sulfate, keratosulfate, chitin, chitosan 1 or chitosan 2.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

(FIG. 1A) $^{35}$S-labeled BW5147 thymoma cells were incubated on HA-coated plates (0.1 μg/ml) that had been pretreated with the indicated peptides (500 μg/ml). Data shown are the means+/−S.D. of % binding from quadruplicate samples. (FIG. 1B) FITC-conjugated HA (0.3 μg/ml) was preincubation with the indicated peptide (500 μg/ml) and examined for binding to BW5147 thymoma cells. Data shown are the binding of FITC-conjugated HA in the presence of the indicated peptides (closed histograms) as compared to the background autofluorescence levels (open histograms).

(FIG. 4A) B16-F10 melanoma cells were suspended ($4 \times 10^5$ cells/ml) in PBS containing Pep-1 monomer (2 or 3 mg/ml) (circles) or 2% DMSO alone (triangles). C57BL/6 mice received i.v. injection of these cell suspensions (500 μl/animal) and were examined for survival. Data shown are the cumulative survival curves from four independent experiments (n=37 for Pep-1 and n=20 for PBS control). Statistically significant difference (p<0.01 by the log-rank test) was observed between the two panels. (FIG. 4B) B16-F10 melanoma cells ($1 \times 10^5$ cells/animal) were s.c. injected into the back of C57BL/6 mice. Pep-1 or RP (40 μg/injection) was injected locally into the tumor inoculation sites 0. 3. and 6 days after tumor injection. Data shown are the means+/−s.e.m. (n=10) of tumor sizes and tumor weights measured 10 days after tumor inoculation. (FIG. 4C) B16-F10 melanoma cells ($2 \times 10^5$ cells/well) were cultured in the presence of the indicated concentrations of Pep-1 (closed circles) or PR (open circles). Data shown are the means+/−s.e.m.(n=3) of $^3$H-thymidine uptake at 24 hr.

(FIG. 5A) 96 well plates were coated with biotinylated-HA (0.1 μg/ml) and pretreated with 500 μg/ml of Pep-1 (open circles), RP (closed circles), or PBS alone (triangles) for 3 hours. These plates were then incubated for 30 min in the presence of HAase (from bovine testis). After extensive wash, the amounts of remaining biotinylated HA on the plates were determined by addition of streptavidin-alkaline phosphatase followed by p-nitrophenyl phosphate substrate. The % HA digestion was calculated from the optical densities. The data shown are the means+/−s.e.m.from triplicate samples analyzed with a hyperbolic model. (FIG. 5B) The impact of Pep-1 on HA digestion and on cell adhesion was examined in parallel using the HA-coated plates prepared simultaneously. Pep-1, RP, or PBS alone was added to the HA-coated plates as above and their effects on HAase-mediated HA degradation and on the adhesion of $^{35}$S-labeled BW5147 thymoma cells were compared. The data shown are the means+/−s.e.m.(n=3) of 50% inhibition doses of HAase (left) and % cell adhesion (right). Pep-1 showed significant ($p<0.01$ by ANOVA) inhibition of cell adhesion, but not of HA digestion. (FIG. 5C) Low molecular weight HA fragments were prepared by sonication of HMW HA followed by overnight digestion with HAase at 37° C. The resulting HA fragments (50 μg/ml) were pre-treated for 3 hours at 37° C. in RPMI medium containing 0.5% DMSO with or without Pep-1 or RP (500 μg/ml) and then added to the XS52 DC cultures ($5 \times 10^5$ cells/ml). Culture supernatants collected 48 hr later were examined for the indicated cytokines by ELISA. Results are expressed as the means+/−s.e.m.from triplicate samples.

(FIG. 6A) Epidermal cells isolated from BALB/c mice at 17 hr after topical application of 0.5% DNFB or vehicle alone were double-stained with FITC-conjugated anti-IA mAb and PE-conjugated anti-CD86 mAb. Data shown are representative two-color FACS profiles, documenting marked elevated surface expression of CD86 by IA$^+$ epidermal cells (i.e., LC) after DNFB application. (FIG. 6B) BALB/c mice received subcutaneous two local injections of Pep-1 or RP (40 μg/injection/ear) 24 and 3 hours before topical application of 0.5% DNFB and epidermal cells were isolated 17 hr later to examine the expression levels of CD86 on LC. Data shown are representative two-color FACS profiles, indicating that DNFB-induced CD86 up-regulation in IA$^+$ LC is prevented by locally administered Pep-1. (FIG. 6C) Graphical representation of the % CD86$^+$ cells/IA$^+$ LC from three independent experiments described in (FIG. 6B) with circles, triangles, and squares showing corresponding pairs in each experiment. Bars represent the mean values (n=3) and the asterisk indicates statistically significant difference between the Pep-1 and the RP panels (*$p<0.03$ by the Mann-Whitney U test).

(FIG. 7A) XS52 DC ($0.2 \times 10^6$ cells/well) were cultured in the presence or absence of the KLH-reactive CD4$^+$ Th1 clone HDK-1 ($0.2 \times 10^6$ cells/well) and/or KLH (100 μg/ml). Culture supernatants collected at 24 hrs were examined for the indicated cytokines by ELISA. Data shown are the means+/−s.e.m. from triplicate samples. (FIG. 7B) XS52 DC and HDK-1 T cells were co-cultured with KLH in the presence of the indicated concentrations of Pep-1. Culture supernatants collected at 24 hrs were examined for the indicated cytokines by ELISA. (FIG. 7C) CD4$^+$ T cells isolated from DO11.10 transgenic mice ($5 \times 10^4$ cells/well) were co-cultured with the indicated numbers of splenic DC isolated from BALB/c mice and the OVA peptide (2 μg/ml) in the presence of 500 μg/ml of Pep-1 (open circles), RP (triangles), or DMSO alone (closed circles). Co-cultures of CD4$^+$ T cells and DC in the absence of OVA peptide served as a control (square). All the cultures were examined for $^3$H-thymidine uptake on Day 3. Data shown are the means+/−s.d. from triplicate samples.

DESCRIPTION OF ILLUSTRATIVE EMBODIMENTS

Figure 1:
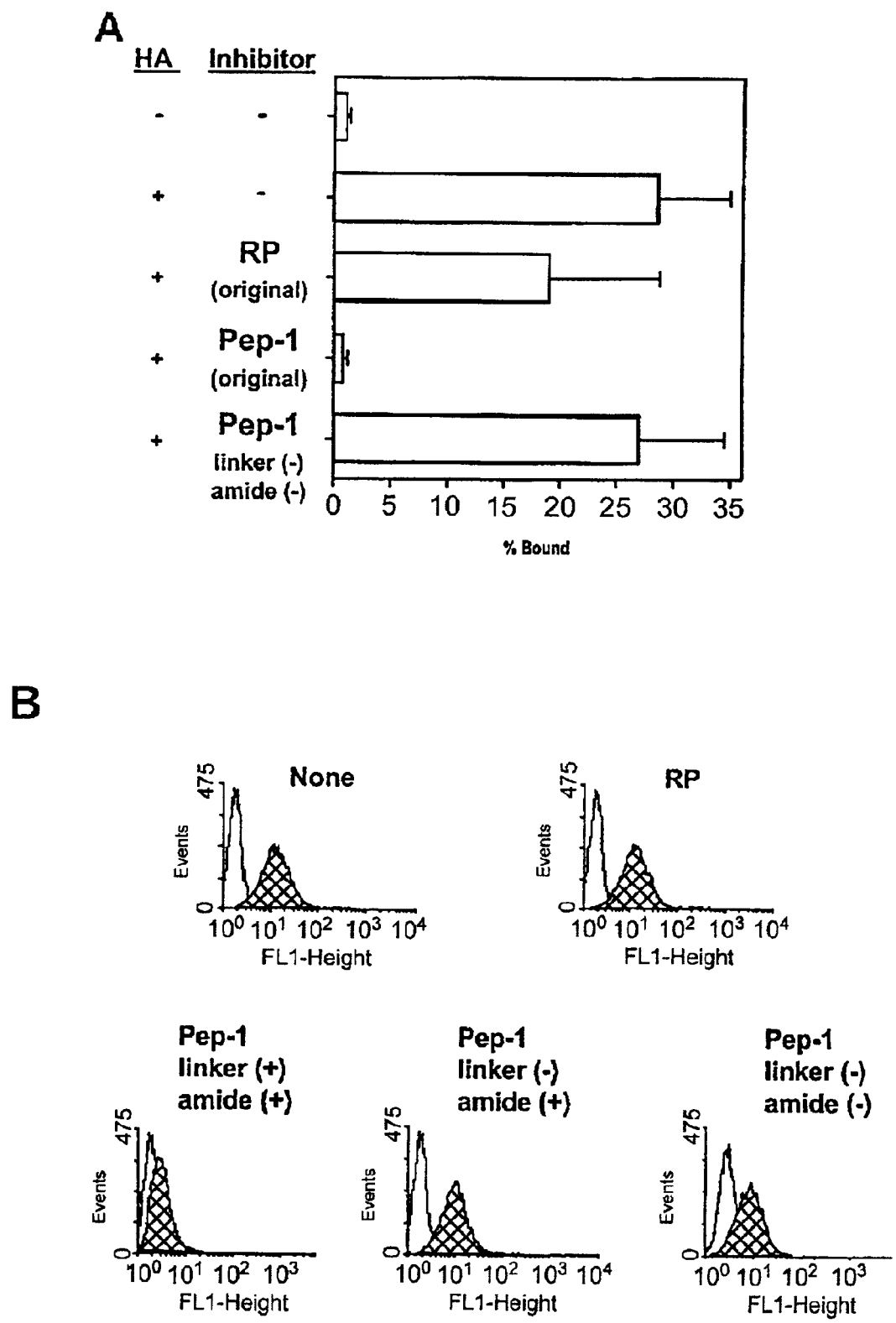
FIGS. 1A–B.

Agents that bind glycosaminoglycans such as chondroitin sulfate, chondroitin sulfate C, dermatan sulfate, heparin, keratan sulfate, keratosulfate, chitin, chitosan 1, chitosan 2 and especially hyaluronic acid (HA) can be useful therapeutic agents given the vast number of physiological processes and pathologies that involve glycosaminoglycans. The present inventors have previously isolated, by phage display technology, peptides that bind to glycosaminoglycans (see co-pending U.S. Provisional Serial No. 60/126,475, incorporated herein in its entirety by reference; and Mummert et al. *J. Exp. Med.* 192:769–779, 2000). All references, to the extent that they provide exemplary procedural or other details supplementary to those set forth herein, are specifically incorporated herein by reference in their entirety.

In one example, co-pending U.S. Provisional Serial No. 60/126,475 describes, the development of a novel peptide that binds glycosaminoglycans, termed "Pep-1," by using phage display technology. This peptide has the sequence GAHWQFNALTVR. Pep-1 showed specific binding to soluble, immobilized, and cell-associated forms of HA, and inhibited leukocyte adhesion to HA substrates almost completely. Systemic, local, or topical administration of Pep-1 inhibited the expression of contact hypersensitivity responses in mice by blocking skin-directed homing of inflammatory leukocytes. Pep-1 also inhibited the sensitization phase by blocking hapten-triggered migration of Langerhans cells (LCs) from the epidermis. These observations document that HA plays an essential role in "two-way" trafficking of leukocytes to and from an inflamed tissue, and thus provides HA inhibitors as therapeutic agents for inflammatory disorders.

The present invention provides derivatives of peptides that bind to glycosaminoglycans with a binding affinity $K_a$ of $5\times10^5$ l/mol or more relative to a naturally occurring glycosaminoglycan in situ, and further shows that the invention the molecules can be used to manipulate many aspects of the immune system, such as cytokine release, antigen presentation, clonal expansion of T-cells, maturation of antigen-presenting cells (APCs) such as dendritic cells, APC-T cell cluster formation, T-cells activation, cell adhesion and leucocyte extravasation. The invention can also be used to manipulate tumorigenesis, particularly metastasis. The derivatives include multimers and/or chemically modified derivatives that have surprisingly improved biological, chemical, and physical properties. For example, multimeric Pep-1 derivatives, especially a Pep-1 dimer and a Pep-1 tetramer, that have greater solubility, stability, and biological activity as compared to Pep-1 are provided. It is envisioned that a variety of different multimers, in addition to those exemplified herein, will exhibit improved properties as compared to monomers, and may even provide synergistic improvement as compared to a comparable number of monomers.

The artificial peptide multimers of the invention preferably bind glycosaminoglycans with a binding affinity of at least $K_a$ of $5\times10^5$ l/mol of more, preferably a $K_a$ of $1\times10^6$ l/mol or more, more preferably a $K_a$ of $1\times10^7$ l/mol or more, or even more preferably a $K_a$ of $1\times10^8$ l/mol or more, $1\times10^9$ l/mol or more, $1\times10^{10}$ l/mol or more, $1\times10^{11}$ l/mol or more in vivo, in vitro, in situ, or under standard laboratory experimental conditions for measuring binding affinity. Binding may be to any gycosaminoglycan, preferably hyaluronic acid.

The invention also provides methods for preparing derivatives of the peptide-inhibitors of glycosaminoglycans. In one embodiment, Pep-1 multimerization can be accomplished by methods that involve succinic acid bridging, PEG-conjugation, use of various linkers or linking agents, as well as using other reagents that can bridge or chemically mediate multimer formation. For example, a Pep-1 dimer was prepared by succinic acid bridging and a Pep-1 tetramer was prepared by PEG-conjugation. In addition to the dimer and the tetramer, the inventors contemplate that multimers including, trimers, pentamers, hexamers, etc., of Pep-1 also will have potent biological activities. The peptide multimer derivatives of the invention are contemplated to comprise two or more peptide subunits, each subunit comprising between 6 and 30 amino acids. In addition, the inventors also contemplate that the multimers can comprise both identical as well as heterogeneous peptide subunits.

Also provided are derivatives of the peptides of the invention that are obtained by chemical modifications. For example, the peptides can be amidated, PEGylated, acetylation, glycosylated, phosphorylated, carboxylation, carbonylation, or extended by attaching extension sequence. In one embodiment, the extension sequence comprises arginine residues. Other types of extension sequences are also contemplated. In some embodiments the extension sequences may be a linker sequence. It is also contemplated that in some cases the peptides of the invention will be derivatized by one or more of the various chemical modification methods and/or the multimerization methods.

The present inventors have also demonstrates anti-cancer properties of the peptide-inhibitors of glycosaminoglycans. For example, the Pep-1 monomer inhibited lung metastasis of melanoma. Thus, the invention envisions anti-cancer therapies, especially those aimed at prevention of tumor metastasis, using peptide-inhibitors of glycosaminoglycans including Pep-1 and its other chemical derivatives. The invention also envisions the use of monomer and tetramer peptide-inhibitors of glycosaminoglycans in cancers involving increased glycosaminoglycans or other glycosaminoglycan related-events.

The peptide-inhibitors of glycosaminoglycans also inhibit interactions of antigen presenting cells with T-cells. For example, the Pep-1 monomer and the Pep-1 tetramer inhibit interaction of dendritic cells (DC) with T cell in vitro. More specifically, Pep-1 and its derivatives inhibit DC-dependent activation of naive T cells as measured by the proliferative responses of CD4$^+$ T-cells freshly isolated from DO11.10 transgenic mice to splenic DC pulsed with ovalbumin (OVA) peptide. Pep-1 and its derivatives also interfere with antigen presentation to memory T cells as seen in experiments with a HDK-1 T-cell clone. These results demonstrate that Pep-1 and its derivatives suppress immune responses not only by blocking HA-dependent, two-way trafficking of leukocytes but also by interfering with DC-dependent presentation of antigens to both naive T-cells (DO11.10) and memory T-cells (HDK-1 T cell clone). In addition, the invention demonstrates that Pep-1 and its derivatives inhibit the secretion of cytokines such as interferon-γ, IL-6, and TNFα in a co-culture system comprising of the XS52 DC line, the HDK-1 T-cell clone, and an antigen, such as the keyhole limpet hemocyanin (KLH) antigen.

Thus, in light of the above, the peptide inhibitors of glycosaminoglycans, including Pep1 and its derivatives, are involved in various aspects of immune system function including, the control of activation, differentiation, proliferation, trafficking, release of cytokines and other regulatory/effector molecules by immune cells. Therefore, it is contemplated that the peptide inhibitors of gylcosaminoglycans will be effective therapeutic agents in a variety of immune disorders. For example, Pep-1 and its derivatives are potent anti-inflammatory molecules by their ability to suppress immune system and more specifically by their ability to prevent leukocyte trafficking. Preventing leukocyte trafficking to and from sites of inflammation prevents the associated tissue damage.

Over the last a few years, there has been accumulating evidence to support the new concept that degradation products of HA (i.e., HA fragments), just like fragments of other extracellular matrix components (e.g., collagens and fibronectin), act as pro-inflammatory mediators. The present inventors have demonstrated that HA fragments trigger IL-6 and TNFα production by the XS52 DC line. In addition, the inventors have demonstrated that the glycosaminoglycan peptide-inhibitors of the invention, including Pep-1 and its derivatives, significantly block the production of both cytokines by XS52 cells following stimulation with HA fragments. Thus, Pep-1 and its derivatives demonstrate pharmacological activities that suppresses immune responses. The inventors therefore contemplate methods for treatment of immune disorders such as inflammatory diseases, autoimmune diseases, and transplantation related graft versus host diseases by administering to a patient in need thereof Pep-1 and its derivatives as well as other glycosaminoglycan inhibitors. Also contemplated are methods for analyzing the biological activities of HA fragments and HA metabolism utilizing the DC lines.

The inventors also have detected, using RT-PCR methods, mRNA for hyaluronidases and for hyaluronan synthases in keratinocytes. Several enzymes involved in HA metabolism were found to be expressed by the Pam 212 keratinocyte line and in mouse skin. This implies that keratinocytes and other skin cells can potentially produce HA fragments in response to environmental stimuli. Thus, the inventors envision pharmaceutical compositions of glycosaminoglycan peptide-inhibitor conjugates invention for topical therapeutic application to neutralize the pro-inflammatory activities of HA and locally produced HA fragments. Hyaluronases are one class of inhibitor that may be used in this context. Other agents that cause HA degradation can be identified using standard screening assays.

Furthermore, the inventors have shown that HA is involved in T cell communication and proliferation and is able to activate naive T cells. These effects can be inhibited by the molecules of the invention, demonstrating that the molecules of the invention can be utilized to inhibit a wide range of gylcosaminoglycan-related reactions.

A more detailed discussion of these embodiments is provided in the following pages.

A. Peptides

The peptides of the invention comprise those peptides that bind to glycosaminoglycans, or fragments thereof, and thereby modulate their function. The peptides are contemplated to comprise between 6 and 30 amino acid residues, and include multimeric derivatives as well as those formed by chemical modifications. The invention also encompasses non-peptide analogs of the peptides, such as mimetics. Such derivatives and analogs are functionally active, i.e., capable of inhibiting one or more functions associated glycosaminoglycan signaling. For example, peptides, derivatives or analogs can reduce immune reaction, prevent/reduce an inflammatory reaction, inhibit antigen presenting cell-T cell interaction, inhibit leukocyte trafficking, and inhibit tumor metastasis.

In addition, derivatives of the peptides of the invention can be chemically synthesized using of a peptide synthesizer and standard synthetic procedures. For example, peptides can be synthesized on a solid support (resin) using either Boc or Fmoc chemistries. Any type of automated synthesizer may be used including batch synthesizers and a continuos-flow synthesizers. Alternatively, a manual synthetic approach may be used to prepare the peptides of the invention. Alternatively, solution phase peptide synthesis methods can also be used.

In one embodiment, the peptide will have the core sequence of general formula $(Z)_n X(Y)_m$, where X is any amino acid and each of Y and Z is an aliphatic or polar aliphatic amino acid, X is any amino acid and n and m are 6 to 30. A more specific embodiment is GAXWQFXALTVX (SEQ ID NO:1), wherein X is any amino acid. Additions to these sequences can comprise extension sequences at either the C-terminal or N-terminal ends. In one embodiment, this extension sequence is a C-terminal extension of $W_p$ where W is any basic or neutral amino acids, and p is 3–13. In another embodiment the extension sequence is made of glycine repeats. In a specific embodiment, the sequence is GAHWQFNALTVR (SEQ ID NO:2). In particular embodiments, the R residue may be substituted by with alanine. Further embodiments subunits comprising the sequence of SEQ ID NO 16, or SEQ ID NO:17.

The invention also contemplates, peptide derivatives that can be made by altering the core sequences by substitutions, additions or deletions that provide for functionally equivalent molecules. For example, some substitution derivatives contemplated include, but are not limited to, those containing, as a primary amino acid sequence, all or part of the amino acid sequence of the peptide with one or more amino acid residues substituted by another amino acid of a similar polarity which acts as a functional equivalent, resulting in a silent alteration.

Substitutes for an amino acid within the sequence may be selected from other members of the class to which the amino acid belongs. For example, the nonpolar or hydrophobic amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged or basic amino acids include arginine, lysine and histidine and negatively charged or acidic amino acids include aspartic acid and glutamic acid.

Furthermore, if desired, non-classical amino acids or chemical amino acid analogs can be introduced as a substitution or addition into the peptide sequence. Non-classical amino acids include but are not limited to the D-isomers of the common amino acids, α-amino isobutyric acid, 4-aminobutyric acid, 2-amino butyric acid, γ-amino butyric acid, ε-6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be either of the optical isomers, D (dextrorotary) or L (levorotary).

The peptide derivatives and analogs of the invention can be produced by various methods known in the art. Typically the basic peptide will be synthesized as the size of the peptides is suitable for artificial synthesis. However, one may also obtain the core peptide sequence by recombinant DNA methods by any of numerous strategies known in the art (Sambrook et al. *Molecular Cloning: A Laboratory Manual*, 2nd Ed. (1989) Cold Spring Harbor Press, Cold Spring Harbor, N.Y.). The sequence can be cleaved at appropriate sites with restriction endonuclease(s), followed by further enzymatic modification if desired, isolated, and ligated in vitro. This product can then be subjected to chemical or enzymatic derivatization methods.

Chemical modification of the peptide sequences include glycosylation, acetylation (including N-terminal acetylation), carboxylation, carbonylation, phosphorylation, PEGylation, amidation, use of non-peptide bonding (e.g., trans olefins), substitution of α-hydrogens with methyl groups, derivatization by known protecting/blocking groups, circularization, inhibition of proteolytic cleavage (e.g., using D amino acids), linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$, acetylation, formylation, oxidation, reduction, etc.

As used herein "PEP 1" encompasses polypeptides having sequence similarity or sequence identity to SEQ ID NO:1 and polypeptide related to SEQ ID NO:1, such as SEQ ID NO:2, polypeptides comprising the sequence $(Z)_n X(Y)_m$, wherein X is any naturally occurring amino acid and Z and Y are each independently selected from the group consisting of aliphatic amino acids and polar aliphatic amino acids, n and m are each independently an integer in the range of from 6 to 30, and wherin the peptide multimer has a binding affinity $K_a$ of $5\times10^5$ l/mol or more relative to a naturally occurring glycosaminoglycan in situ. PEP 1 also encompases polypeptides of the formula ZZZXZZZ wherein Z is an amino acid selected from the group consisting of aliphatic and polar aliphatic residues, and wherein X is any amino acid. The subunit may further comprises an N- or C-terminal extension $W_p$, wherein W is any basic or neutral amino acid, and p is an integer between 3 and 13, for example, wherein W is arginine or glycine independently. The peptide subunit also may comprise a terminal serine. In a particular embodiment, the extension is a C-terminal GGGS. PEP 1 can have of at least about 65%, preferably at least about 80%, more preferably at least about 85%, and can be about 90%, 91%, 92%, 93%, 94%, 95%, 96%, 97%, 98%, 99% or more identity to SEQ ID NO:1 or 2. Sequence similarity and sequence identity are calculated based on a reference sequence, which will be at least about 6 amino acids long, more usually at least about 10 amino acids long, and may extend to the complete sequence that is being compared. In general, percent sequence identity is calculated by counting the number of residue matches (e.g., nucleotide residue or amino acid residue) between the query and test sequence and dividing total number of matches by the number of residues of the individual sequences found in the region of strongest alignment. Thus, where 10 residues of an 11 residue query sequence matches a test sequence, the percent identity above would be 10 divided by 11, or approximately, 90.9%. Algorithms for computer-based sequence analysis are known in the art, such as BLAST (see, e.g., Altschul et al., *J. Mol. Biol.*, 215:403–10 (1990)), particularly the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

1. Linkers/Coupling Agents/Extensions

In preparing peptide multimers of the present invention, one may use a variety of linking or coupling agents. For example, one can join individual peptide subunits to form multimers using a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Additionally, while numerous types of disulfide-bond containing linkers are known which can successfully be employed to conjugate moieties, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moiety prior to binding at the site of action.

Additionally, any other linking/coupling agents and/or mechanisms known to those of skill in the art can be used to combine the peptides of the present invention, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

Cross-linking reagents are used to form molecular bridges that tie together functional groups of two different molecules, e.g., a stabilizing and coagulating agent. However, it is contemplated that dimers or multimers of the same analog/protein subunit can be made or that heteromeric complexes comprised of different analogs/protein subunits can be created. To link two different compounds in a step-wise manner, hetero-bifunctional cross-linkers can be used that eliminate unwanted homopolymer formation. Table 1 provides a list of hetero-bifunctional cross-linkers.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional

TABLE 1

HETERO-BIFUNCTIONAL CROSS-LINKERS

| Linker | Reactive Toward | Advantages and Applications | Spacer Arm Length After Cross-Linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

These other cross-linking agents can also be used to link extension sequences to the peptides of the invention. For example, one can link an extension peptide sequence to the terminal ends of the peptides of the invention, i.e., at the C-terminal end and/or at the N-terminal end. Thus, any peptide sequence, or motif can be linked to the peptides of the invention using a suitable linking agent.

2. Chemical Modifications

Other methods for obtaining the peptide derivatives of the invention involve chemical modifications. The peptide compositions can be modified by amidation, PEGylation, glycosylation, acetylation, prenylation, phosphorylation, biotinylation, carboxylation, carbonylation, or may be further derivatized by addition of known protecting/blocking groups. These chemical modifications can be made by methods well known to the skilled artisan. Alternatively, one can also use enzymes to achieve such modifications. For example, any kinase enzyme can be used for phosphorylation, specifically serine-threonine kinase enzymes phosphorylate serine or threonine residues and tyrosine kinases may be used to phosphorylate tyrosine residues in the peptide.

One can also derivatize peptides by adding or attaching a non-peptide ligand. The ligand may comprise of, but is not limited to, an acetamido, an acetoacetamido, an acetoacetyl, an acetonyl, an acetonylidene, an acetyl, an acrlyl, an adipyl, an alanyl, a beta-alanyl, an allophanoyl, an allyl, an allylidene, an amidino, an amino, an amyl, an anilino, an anisidino, an anisyl, an anthranoyl, an arsino, an azelaoyl, an azido, an azino, an azo, an azoxy, a benzal, a benzamido, a benzhydryl, a benzimido, a benzoxy, a benzoyl, a benzyl, a benzlidine, a benzyldyne, a biphenylyl, a biphenylene, a bromo, a butoxy, a sec-butoxy, a tert-butoxy, a butyl, an iso-butyl, a sec-butyl, a tert-butyl, a butyryl, a caproyl, a capryl, a caprylyl, a cabamido, a cabamoyl, a cabamyl, a cabozoyl, a carbethoxy, a cabobenzoxy, a carbonyl, a carboxy, a cetyl, a chloro, a chloroformyl, a cinnamyl, a cinnamoyl, a cinnamylidene, a cresyl, a crotoxyl, a crotyl, a cynamido, a cyanato, a cyano, a decanediol, a decanoly, a diazo, a diazoamine, a disilanyl, a disiloxanoxy, a disulfinyl, a dithio, an enanthyl, an epoxy, an ethenyl, an epoxy, an ethenyl, an ethinyl, an ethyl, an ethylthio, a fluoro, a fluorenyl, a formamido, a formyl, a fumaroy, a furfuryl, a furfurylidene, a furyl, a glutamyl, a gularyl, a glycidyl, a glycinamido, a glycolyl, a glycyl, a glyoxylyl, a guanidino, a guanyl, a heptadecanoyl, a heptanamido, a heptanedioyl, a heptanoyl, a hexadecanoyl, a hexamethylene, a hexanedioyl, a hippuryl, a hydantoyl, a hyrazino, a hydrazo, a hydrocinnamoyl, a hydroperoxy, a hydroxamino, a hydroxy, an imino, an indenyl, an iodoso, an isoamyl, an isobutenyl, an isobutoxy, an isobutyl, an isobutylidene, an isobutyryl, an isocyanato, an isocyano, an isohexyl, an isoleucyl, an isonitroso, an isopentyl, an isopentylidene, an sopropenyl, an isopropoxy, an isopropl, an isopropylidene, an isothiocyanato, an isovaleryl, an iodo, a keto, a lactyl, a lauroyl, a leucyl, a levulinyl, a malonyl, a mandelyl, a mercapto, a methacrylyl, a methallyl, a methionyl, a methoxy, a methyl, a methylene, a methylenedioxy, a methylenedisulfonyl, a methylol, a methylthio, a myristyl, a naphthal, a naphthobenzyl, a naphthoxy, a naphthyl, a naphthylidene, a neopentyl, a nitramino, a nitro, a nitrosamino, a nitrosimino, a nitroso, a nonanoyl, an oleyl, an oxalyl, an oxamindo, an oxo, a palmityl, a pelargonyl, a pentamethylene, a pentyl, a phenacyl, a phenacylidene, a phenanthryl, a phenethyl, a phenoxy, a phenyl, a phenylene, a phenylenedioxy, a phosphino, a phosphinyl, a phospho, a phosphono, a phthalyl, a picryl, a pimely, a piperdino, a pieridyl, a pipemoyl, a pivalyl, a prenyl, a propargyl, a propenyl, a iso-propenyl, a propionyl, a propoxy, a propyl, a iso-propyl, a propylidene, a pyridino, a pyrryl, a salicyl, a selenyl, a seryl, a siloxy, a silyl, a silylene, a sorbyl, a stearyl, a styryl, a suberyl, a succinamyl, a succinyl, a sulfamino, a sulfamyl, a sulfanilyl, a sulfeno, a sulfhydryl, a sulfinyl, a sulfo, a sulfonyl, a terephthalyl, a tetramethylene, a thenyl, a thienyl, a thiobenzoyl, a thiocarbamyl, a thiocarbonyl, a thiocarboxy, a thiocyanato, a thionyl, a thiophenacyl, a thiuram, a thronyl, a toluidino, a toluyl, a tolyl, a alpha-tolyl, a tolylene, a alpha-tolylene, a tosyl, a triazano, a trimethylene, a triphenylmethyl, a tyrosyl, a ureido, a valeryl, a valyl, a vinyl, a vinylidene, a xenyl, a xylidino, a xylyl, or a xylylene ligand.

B. Glycosaminoglycan Function and Related Disease States

As glycosaminoglycans are involved in interactions with various cellular receptors, agents that bind and modulate glycosaminoglycans are useful as therapeutic agents in numerous diseases. For example, one of the cellular receptors of HA is CD44 is which is a family of cell-surface glycoproteins generated by alternative splicing and post-translational modification (Aruffo et al. *Cell*. 61:1303–1313, 1990; Lesley et al. *Exp. Cell. Res.* 187:224, 1990; Miyake et al. *J. Exp. Med.* 172:69–75, 1990; Culty et al., *J. Cell. Biol.* 111:2765 1990). Various isoforms of CD44 are expressed by different cell types, such as T cells and B cells, granulocytes, monocytes, macrophages, and DC, including LC. HA-CD44 interaction mediates rolling of leukocytes over endothelial cells, one of the numerous processes that take place in leukocyte homing (DeGrendele et al. *J. Exp. Med.* 183:1119–1130, 1996; Clark et al. et al. *J. Cell. Bio.* 134:1075–1087, 1996). HA-CD44 interaction also is known to mediate many physiological and pathological events, including leukocyte homing, tumor metastasis, tissue development, hematopoiesis, cytokine production, T cell activation, and apoptosis.

Thus, pharmacological formulations of the peptide derivatives of the present invention can be used as therapeutic agents that modulate HA-CD44 interaction, and thus are useful to prevent and/or treat patients with diseases mediated by this interaction. The nature of the modulation may comprise either inhibition or enhancement of the interaction. Some of the diseases that the peptide derivatives provided here are contemplated to be useful in include, contact hypersensitivity and delayed type hypersensitivity reactions (Camp et al. *J. Exp. Med.* 178:497–507, 1993; Verdrengh et al. *Scand. J Immunol.* 42:353, 1995), tumor metastasis (Bartolazzi et al. *J. Exp. Med.* 180:53–66 1994; Guo et al., *Cance.r Res.* 54:1561 1994; Zahalka et al. *J. Immunol.* 154:5345–5355,1995), collagen-induced autoimmune arthritis models (Verdrengh et al. *Scand. J. Immunol.* 42:353, 1995; Mikecz et al. *Nat. Med.* 1:558, 1995; Zeidler et al. *Autoimmunity.* 21:245, 1995). In relation to prevention of tumor metastasis, the present inventors have shown that the peptides of the invention, particularly Pep-1 and its derivatives, inhibit metastasis in a mouse model of malignant cancer.

The present inventors also have previously demonstrated that peptide inhibitors of HA can be used to prevent the induction of immune reactions in the sensitization phase and to inhibit inflammatory reactions in the elicitation phase. For example, Mohamadzadeh et al. *J. Invest. Dermatol.,* 1999 demonstrates that keratinocytes express relatively large amounts of cell-surface HA, and the long-term LC line, XS106, exhibits significant rolling over in HA-coated plates as well as over confluent keratinocyte monolayers under physiological flow conditions. This XS106 cell rolling is blocked by soluble HA and local injection of soluble HA into mouse skin inhibits almost completely LC emigration that is triggered by topical application of DNFB. Thus, the peptides of the present invention are useful to inhibit a mechanism of DC migration, for example, an interaction between HA (on keratinocytes) and CD44 (on activated LC).

In addition to CD44, HA has several other ligands including, RHAMM, aggrecan, versican, link protein, the LEC HA receptor, hyaluronectin, inter-α-trypsin inhibitor-related proteins, BEHAB, CD38, CD54, and hyaluronidase (HAase). Therefore, the peptide derivatives that bind glycosaminoglycans, provided herein, are envisioned to be useful in potentiating or inhibiting glycosaminoglycan-mediated activities through these receptor molecules as well. The skilled artisan will recognize that the peptide derivatives provided here will be useful as therapeutic agents in various pathologies and that the scope of the invention is not limited to the diseases and conditions mentioned here.

C. HA Metabolism

Schiller et al. *J. Biol. Chem.* 218:139–145, 1955, first studied the regional turnover of HA in the skin over forty years ago. Using radioactive tracers, these investigators showed that HA has a physiological half-life of 2–4 days. More recently, Fraser and Laurent (1989), have shown that the bulk of HA is not degraded in the tissue of origin (i.e., regional turnover) but rather is transported to the regional lymph nodes for degradation. HA that escapes degradation in the lymph nodes enters the circulation via the thoracic duct where it is catabolized predominantly by the liver. Three enzymatic reactions are responsible for HA degradation, namely, a) hyaluronidase (HAase), b) β-D-glucuronidase, and c) β-N-acetyl-D-hexosaminidase (Roden et al. *Ciba. Found.Symp.* 143:60–76, 1989). Three unique HAases have been identified in humans to date (Lepperdinger et al. *J. Biol. Chem.* 273:22466–22470, 1998; Gmachl et al. *F.E.B.S. Lett.* 336:545–548, 1993;). HAases degrades HA polysaccharides to oligosaccharides while β-D-glucuronidase and β-N-acetyl-D-hexosaminidase degrades oligosaccharides into monosaccharides (glucuronic acid and N-acetyglucosamine). Glucuronic acid is converted through a series of enzymatic reactions to D-glucose-6-phosphate. The D-glucose-6-phosphate then funnels into the glycolytic pathway. N-acetyglucosamine is phosphorylated in an ATP-dependent reaction to yield N-acetyglucosamine-6-phosphate. The N-acetyglucosamine-6-phosphate is converted to either UDP-N-acetyglucosamine or fructose-6-phosphate. UDP-N-acetyglucosamine serves as starting material for the synthesis of new polysaccharides while fructose-6-phosphate enters the glycolytic pathway (Roden et al. *Ciba. Found. Symp.* 143:60–76, 1989).

Stimuli that directly modulate the enzymatic degradation of hyaluronan remain to be determined. However, Elias and colleagues (Sampson et al. *J. Clin. Invest.* 90:1492–1503, 1992) have shown a correlation between the level of CD44 mRNA and HA degradation in human lung fibroblasts after stimulation with recombinant IL-1 and TNF. These investigators speculated increased expression of CD44 may enhance HA binding and result in increased HA uptake and consequent degradation.

Importantly products of HA catabolism have been associated with biological functions. Recently, Noble and colleagues have shown that HA fragments, either alone or synergistically with cytokines, induce macrophages to elaborate chemokines including MIP-1β, MIP-1α, Mig, interferon-inducible protein-10, RANTES, cytokine responsive gene-2 and monocyte chemoattractant protein-1 (Horton et al. *J. Biol. Chem.* 273:35088–35094, 1998; McKee et al. *J. Clin. Invest.* 98:2403–2413, 1996; Horton et al. *J. Immunol.* 160:3023–3030, 1998; Hodge-Dufour et al. *J. Immunol.* 159:2492–2500, 1997). HA fragments have also been shown to be potent activators of DC and induce phenotypic maturation (up-regulation of MHC class II molecule, CD80, CD86, and CD83 and down-regulation of CD115) and the production of IL-1β, TNFα and IL-12 (Termeer et al. *J. Immunol.* 165:1863–1870, 2000).

Synthesis of new HA polysaccharides is mediated by HA synthases. Like HAases, three synthases have been identified to date (Itano et al. *Biochem. Biophys. Res.Commun.* 222:816–820, 1996; Spicer et al. *J. Biol.Chem.*, 271:23400–23406, 1996; Spicer et al. *J. Biol. Chem.* 272:8957–8961, 1997; Watanabe et al. *J. Biol. Chem.* 271:22945–22948,1996). A variety of stimuli have been shown to initiate HA synthesis, including: a) environmental factors such as irradiation (Li et al. *Am.J.Respir.Cell Mol-.Biol.* 23:411–418. 2000), culturing conditions (Huey et al. *Matrix.* 10:75–83, 1990) and hyperbaric oxygen (Roberts et al. *Br.J.Dermatol.* 131:630–633, 1994), b) HAase-mediated degradation of HA from the plasma membrane surface (Philipson et al. *Biochem.* 24:7899–7906, 1985; Larnier et al. *Biochim.Biophys.Acta.* 1014:145–152, 1989) and, 3) various factors including IL-1β, TNFα, PDGF-AA, PDGF-BB, bFGF, EGF and TGF-β1 (Godden et al. *Eur. J. Cancer.* 35:473–480, 1999; Jacobson et al. *Biochem.J.* 348 Pt 1:29–35, 2000; Kennedy et al. *J. Pediatr. Surg.* 35:874–879, 2000; Ueki et al. *Biochim.Biophys.Acta.* 1495:160–167, 2000; Denk et al. *Curr.Eye. Res.* 20:77–80, 2000).

The present inventors have demonstrated that keratinocytes express mRNA for HA synthase-2 and 3, as well as for HAases-1, 2, and 3, thus, showing that keratinocytes are fully capable of synthesizing and degrading HA actively. The current inventors also have detected the expression of these mRNAs in the skin, which indicates that keratinocytes (and other cell types in the skin, including DC) can potentially produce HA fragments in response to environmental stimuli.

HA fragments have been shown to act as pro-inflammatory mediators. Additionally, the present inventors have demonstrated that HA fragments trigger IL-6 and TNFα production by the XS52 DC line. The inventors have also demonstrated that the glycosaminoglycan peptide-inhibitors of the invention, including Pep-1 and its derivatives, significantly block the production of both cytokines by XS52 cells following stimulation with HA fragments. These observations, among others provide therapeutic methods utilizing the ability of the peptides of the invention to neutralize the pro-inflammatory activities of locally produced HA fragments.

D. Therapeutic Uses

The peptide derivatives of the invention can be used as therapeutic and preventive agents for the treatment of various human and veterinary diseases associated with glycosaminoglycan function. Particular activities of the peptides include, but are not limited to, inhibiting leukocyte migration, inhibiting leukocyte activation, inhibiting cytokine production, inhibiting lymphocyte proliferation, inhibiting lymphocyte differentiation, inhibiting interaction between cells (e.g., between an antigen presenting cell and a T cell), inhibiting dendritic cell migration, reduction of immune reaction, inhibition of dendritic cell migration, inhibition of metastasis, or binding to a glycosaminoglycan and/or fragment thereof. In the context of these applications, it is contemplated that the peptides of the invention will be used either alone or in combination with other therapeutic agents to accomplish these objectives.

Several of the peptide derivatives of the invention are soluble in the absence of solvents and/or are also storage stable in water. In addition, several of the multimeric peptide derivatives in particular have increased half-lives. These properties makes them extremely desirable for therapeutic applications. However, in other instances it may be desirable to further modify the peptides to provide these or other desirable characteristics for therapeutic use.

When used as a therapeutic, an appropriate dosage of the pharmaceutical formulation of the glycosaminoglycan binding agent, or mixture thereof, will be determined by any of several well established methodologies. For instance, animal studies are commonly used to determine the maximal tolerable dose, or MTD, of bioactive agent per kilogram weight. Other toxicity and pharmacokinetic profiles will also be determined. In general, at least one of the animal species tested is mammalian. Those skilled in the art regularly extrapolate doses for efficacy and avoiding toxicity to other species, including human. Additionally, therapeutic dosages may also be altered depending upon factors such as the severity of infection, and the size or species of the host.

Preferably, animal hosts that may be treated using the peptides of the present invention include, but are not limited to, invertebrates, vertebrates, birds, mammals such as pigs, goats, sheep, cows, dogs, cats, and particularly humans.

1. Inflammatory Conditions

As the peptides of the invention are involved in numerous events that lead to inflammatory responses, for e.g., inhibition of leukocyte migration, inhibition of leukocyte activation, inhibition of cytokine production, inhibition of lymphocyte proliferation, inhibition of lymphocyte differentiation, inhibition of interaction between an antigen presenting cell and a T cell, and/or inhibition of dendritic cell migration, etc. these peptides are envisioned to be useful in the treatment and/or prevention of inflammation. For example, responses that inhibit migration of leukocytes to and from sites of inflammation, prevent the associated cellular damage caused by the accumulation and activation of leukocytes at these sites. Thus, patients suffering from a variety of inflammatory diseases including, infections, autoimmune conditions, graft versus host diseases, etc. may be treated with a composition of the invention.

Infections include all types of infections such as but not limited to, viral infections, bacterial infections, fungal infections, burn infections, wound infections, etc. One important use of the glycosaminoglycan-specific peptide inhibitors of the invention is in the treatment, amelioration and/or prevention of HIV infection. HIV and other infectious organisms are known to bind to HA (and other glycosaminoglycans) upon infection of cells. Therefore, peptides of the invention can be used to inhibit these interactions.

Autoimmune disease are exemplified by multiple sclerosis, rheumatoid arthritis, or systemic lupus erythematosus, etc., as non-limiting examples. In addition, peptides of the invention may be useful to prevent autoimmune inflammatory reactions stemming from procedures such as bone marrow and organ transplants, for example, suppression of graft-versus-host disease.

Administration of the anti-inflammatory composition of the invention may be through a variety of routes. For example, one can administer the composition systemically or locally or even topically, e.g., systemic treatment for lupus; injection into a joint to decrease inflammation caused by arthritis; or topical application in the form of a creme, ointment, balm, gel, etc. for an external topical infection. Alternately, where the targeted region of inflammation is internal, preparations of peptides may be provided by oral dosing. Additionally, pulmonary inflammation may be treated both parenterally and by direct application of suitably formulated forms of the peptides to the lung by inhalation therapy or intranasal administration.

In addition to these inflammatory conditions, one may administer a therapeutic anti-HA peptides and their derivatives to patients suffering from a stroke or a myocardial infarction. In patients suffering from a myocardial infarction the peptides of the invention can facilitate a decrease in pressure upon myocardial tissues, prevent tissue necrosis, and relieve edema (Maclean et al. *Science.* 194:199–200, 1976; Opie et al. *Am. Heart. J.* 100:531–52, 1980). Use of peptide inhibitors of HA activity in treatment of myocardial infarct patients is advantageous over use of therapeutic agents such as hyaluronidase (HAase) as the peptide's activity is specific to HA and thus will not be inhibited by heparin. Heparin is often administered during heart attacks and is a very powerful inhibitor of HAase activity of other HAase containing this EGF motif Because the peptide inhibitors of HA are not subject to regulation by heparin, the clinician need not be concerned that co-administration of heparin with the anti-HA peptide.

Peptide derivatives of the invention that inhibit HA activity can also be used in the treatment of edema associated with brain tumors, particularly that associated with glioblastoma multiform. The edema associated with brain tumors results from the accumulation of HA in the non-cancerous portions of the brain adjacent the tumor. Administration of the HA-specific peptide inhibitor to the sites of hyaluronan accumulation (e.g., by intravenous injection or via a shunt) can relieve the edema associated with such malignancies by binding to and preventing activity of excess HA these sites. Thus, HA inhibitors can be successful in the treatment of brain tumors not only in the reduction of the tumor mass and inhibition of tumor growth and/or metastasis (see the section infra for a discussion of the anti-cancer properties of the peptides of the invention), but it also is useful in relieving edema associated with the malignancy.

2. Combination Immunotherapies

The anti-inflammatory therapies comprising the glycosaminoglycan-binding inhibitors of the present invention can be used in conjunction with other therapies that are used for the treatment of inflammation. Thus, one may use a peptide inhibitor of the invention in combination with an anti-inflammatory agent. Anti-inflammatory agents are agents that decrease the signs and symptoms of inflammation. A wide variety of anti-inflammatory agents are known to one of skill in the art. Most commonly used are the nonsteroidal anti-inflammatory agents (NSAIDs) which work by inhibiting the production of prostaglandins. Non-limiting examples include, ibuprofen, ketoprofen, piroxicam, naproxen, naproxen sodium, sulindac, celecoxib, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate. Another group of anti-inflammatory agents comprise steroid based potent anti-inflammatory agents, for example, the corticosteroids which are exemplified by dexamethason, hydrocortisone, methylprednisolone, prednisone, and triamcinolone as non-limiting examples. Several of these anti-inflammatory agents are available under well known brand names, for example, the NSAIDs comprising ibuprofen include Advil, Motrin IB, Nuprin; NSAIDs comprising acetaminophens include Tylenol; NSAIDs comprising naproxen include Aleve.

It is conceivable that more than one administration of either the other anti-inflammatory agent and the peptide of the present invention will be required to achieve complete cure. Thus, various combinations may be employed, where the other anti-inflammatory agent is "A" and the anti-glycosaminoglycan peptide of the present invention is "B", as exemplified below:

| A/B/A | B/A/B | B/B/A | A/A/B | B/A/A | A/B/B | B/B/B/A | B/B/A/B |
|-------|-------|-------|-------|-------|-------|---------|---------|
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations also are contemplated.

3. Cancer Therapies

The present inventors have shown that both the glycosaminoglycan-specific peptide inhibitors (e.g., Pep-1 and its derivatives) as well as the glycosaminoglycan-specific peptide derivatives are useful in the treatment of cancer. Particularly, peptides of the invention, were shown to inhibit metastasis. It is contemplated that the peptides of the invention will be used in the treatment of brain cancer, lung cancer, throat cancer, esophageal cancer, cancer of the head and neck, skin cancer, breast cancer, stomach cancer, colon cancer, cancer of the rectum, cervical cancer, prostate cancer, ovarian cancer, liver cancer, pancreatic cancer, a cancer of the blood, small lung cell carcinoma, squamous lung cell carcinoma, as well as any other cancer associated with increased levels of HA or other glycosaminoglycans or of cancers that are associated with altered glycosaminoglycan functions. It is also contemplated that the peptides of the invention may increase the sensitivity of tumors that are resistant to conventional radiotherapy or chemotherapy. In addition, the invention also contemplates the use of peptide mimetics.

Additionally, another important embodiment of the invention provides, for the first time, a successful anti-cancer effect by altering glycosaminoglycan functions. Thus, the invention envisions anticancer-therapies utilizing any agent that is capable of inhibiting glycosaminoglycan function or expression. Thus, provided are therapies for the treatment of cancers associated with increased levels of HA or other glycosaminoglycans, or of cancers that are associated with altered glycosaminoglycan function, comprising providing to a patient in need thereof a agent that inhibits a glycosaminoglycan. Such an agent can include among others any peptide or non-peptide glycosaminoglycan inhibitor. Non-peptide inhibitors of the invention include naturally occurring products, including those isolated from any living organism; man-made products; chemical compounds; pharmaceutical compounds; peptide mimetics; small molecule inhibitors; compounds that may be designed through rational drug design starting from known inhibitors of glycosaminoglycan; polynucleotides; antisense molecules; ribozymes; antibodies to glycosaminoglycans; etc.

The peptide and non-peptide glycosaminoglycan inhibitors of the invention are contemplated to provide anti-cancer therapy either alone or in combination with other anti-cancer agents. Several cancer-therapies are currently prescribed for the treatment of cancers. Presented in sections below is a discussion of some of these therapeutic methods.

4. Combination Cancer Therapies

A wide variety of cancer therapies, known to one of skill in the art, may be used in combination with the anticancer peptides of the present invention. Thus, in order to increase the effectiveness of the anticancer therapy using a peptide of the present invention it may be desirable to combine these compositions with other agents effective in the treatment of cancer such as but not limited to those described below.

For example, one can use the peptide inhibitors of glycosaminoglycans of the invention for cancer therapy in conjunction with surgery and/or radiation therapy and/or chemotherapy, and/or gene therapy, and/or local heat therapy. All other non-peptide inhibitors based cancer therapies are referred to herein as "other cancer therapies."

The other cancer therapy may precede or follow the peptide-inhibitor-based therapy by intervals ranging from minutes to days to weeks. In embodiments where the other cancer therapy and the peptide-inhibitor-based therapy are administered together, one would generally ensure that a significant period of time did not expire between the time of each delivery. In such instances, it is contemplated that one would administer to a patient both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the other cancer therapy and the peptide-inhibitor-based therapy will be required to achieve complete cancer cure. Various combinations may be employed, where the other cancer therapy is "A" and the peptide-inhibitor-based therapy treatment is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other Combinations also are Contemplated.

In addition, the peptide-inhibitor-based therapy can be administered to a patient in conjunction with other therapeutic methods such as for example standard AIDS treatments. The exact dosages and regimens can be suitable altered by those of ordinary skill in the art. Examples of cancer therapies are presented below.

a) Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiation. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

b) Surgery

Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue. Upon excision of part of all of cancerous cells, tissue, or tumor, a cavity may be formed in the body. Treatment may be accomplished by perfusion, direct injection or local application of the area with an additional anti-cancer therapy, such as with peptides of the invention. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

c) Chemotherapeutic Agents

Agents that affect DNA function are defined as chemotherapeutic agents, for example, agents that directly cross-link DNA, agents that intercalate into DNA, and agents that lead to chromosomal and mitotic aberrations by affecting nucleic acid synthesis. Some examples of chemotherapeutic agents include antibiotic chemotherapeutics, such as Doxorubicin, Daunorubicin, Mitomycin (also known as mutamycin and/or mitomycin-C), Actinomycin D (Dactinomycin), Bleomycin, and Plicomycin; Plant alkaloids such as Taxol, Vincristine, and Vinblastine; miscellaneous agents such as Cisplatin, VP16, Tumor Necrosis Factor; alkylating agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine; and other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Navelbine, Famesyl-protein transferase inhibitors, Transplatinum, 5-Fluorouracil, and Methotrexate, Temazolomide (an aqueous form of DTIC), or any analog or derivative variant of the foregoing.

d) Gene Therapy

In yet another embodiment, the other treatment is a gene therapy in which a therapeutic polynucleotide is administered before, after, or at the same time as a peptide(s) of the invention is administered. Appropriate genes for use according to this embodiment are genes encoding tumor suppressors (p53, Rb, p16), antisense oncogenes (ras, myc, erb), inducers of apoptosis (Bcl-2, Bax) and other such genes.

e) Other Therapies

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. In other embodiments, cytostatic or differentiation agents can be used in combination with the present invention to improve the anti-hyperproliferative efficacy of the treatments.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastasis.

5. Other Therapeutic Uses

The peptides of the invention may also be useful as a form of contraception, since HA is known to mediate binding of the sperm to the oocyte. Peptides that inhibit HA may inhibit binding between the sperm and the oocyte, since such binding requires HA-mediated binding, thus effectively prevent fertilization, thus effectively preventing formation of the zygote.

E. Targeting Conjugates Comprising Glycosaminoglycan Binding Peptides

Targeting other therapeutic agents to sites of inflammation that are characterized by HA fragments by conjugation to a peptide derivative of the invention is another ways to use the peptides of the invention in the therapeutic intervention of inflammation, cancer, or other immune diseases. The agent may be conjugated by a covalent bond or a releasable bond. Several different therapeutic agents are contemplated depending on the disease the agent is used for. For the treatment of a cancer a radionuclide or a cancer chemotherapeutic agent may be conjugated to a peptide of the invention. The peptide of the invention may be also conjugated to a toxin, for example, ricin A chain, cholera toxin, pertussis toxin, etc. Alternatively the present invention anticipates the use of an hyaluronidase to reduce the levels of HA.

In other examples, immunocancer therapy is contemplated, where an immune effector is conjugated or linked to a peptides of the invention to target and destroy cancer cells. The immune effector may be, for example, an antibody specific for some marker on the surface of a tumor cell. The antibody alone may serve as an effector of therapy or it may recruit other cells to actually effect cell killing. Alternatively, the effector may be a lymphocyte carrying a surface molecule that interacts, either directly or indirectly, with a tumor cell target. Various effector cells include cytotoxic T cells and NK cells.

In addition, it is contemplated that one may conjugate a diagnostic agent to a peptide of the invention and target this to a cancer cell. In context of cancers the diagnostic agent can be agent used to image tumors, for example, through magnetic resonance imaging, x-ray imaging, computerized emission tomography and the like. Elements particularly useful in Magnetic Resonance Imaging ("MRI") include the nuclear magnetic spin-resonance isotopes $^{157}$Gd, $^{55}$Mn, $^{162}$Dy, $^{52}$Cr, and $^{56}$Fe, with gadolinium often being preferred. Radioactive substances, such as technicium$^{99m}$ or indium$^{111}$, that may be detected using a gamma scintillation camera or detector, also may be used. Further examples of metallic ions suitable for use in this invention are $^{123}$I, $^{131}$I, $^{131}$I, $^{97}$Ru, $^{67}$Cu, $^{67}$Ga, $^{125}$I, $^{68}$Ga, $^{72}$As, $^{89}$Zr, and $^{201}$Tl.

In the context of inflammatory diseases one may conjugate any other anti-inflammatory agent (see examples in the sections above) to obtain an enhanced anti-inflammatory response.

F. Pharmaceutical Preparations and Modes of Administration

Pharmaceutical compositions of the present invention comprise an effective amount of one or more peptide derivative that binds to and modulates the function of a glycosaminoglycan or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one peptide derivative of the invention or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., Mack Printing Company, 1990, pp. 1289–1329, incorporated herein by reference). Except insofar as any conventional carrier is incompatible with the active ingredient, its use in the therapeutic or pharmaceutical compositions is contemplated.

The pharmaceutical formulations of the peptides of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The peptides of the invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g. triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the peptides of the invention are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof G. Screening for Compounds that Alter Glycosaminoglycan Metabolism The present invention further comprises methods for identifying modulators of glycosaminoglycan metabolism. These assays may comprise random screening of large libraries of candidate substances; alternatively, the assays may be used to focus on particular classes of compounds selected with an eye towards structural attributes that are believed to make them more likely to modulate glycosaminoglycan metabolism.

By metabolism, it is meant that one may assay for changes in glycosaminoglycan synthesis, degradation, transport, or binding. To identify a modulator, one generally will determine the metabolism of glycosaminoglycans in the presence of the candidate substance on a cell, tissue, organ or organism, as compared to metabolism in the absence of the candidate substance, a modulator defined as any substance that alters metabolism. For example, a method generally comprises: providing a candidate modulator; admixing the candidate modulator with a cell, tissue or a suitable experimental animal; measuring one or more aspects of glycosaminoglycan metabolism in the tissue cell or animal in step; and comparing the aspect measured in step (c) with the aspect of the cell, tissue or animal in the absence of said candidate modulator, wherein a difference between the aspect indicates that said candidate modulator is, indeed, a modulator of glycosaminoglycan metabolism.

Assays may be conducted in cell free systems as well.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may potentially modulate glycosaminoglycan metabolism. The candidate substance may be a protein or fragment thereof, a small molecule, or even a nucleic acid molecule. It may prove to be the case that the most useful pharmacological compounds will be compounds that are structurally related to glycosaminoglycans themselves. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotypic would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on glycosaminoglycan production. Regardless of the type of inhibitor or activator identified by the present screening methods, the effect of the inhibition or activator by such a compound results in an alteration in glycosaminoglycan function as compared to that observed in the absence of the added candidate substance.

2. In vitro Cell Free Assays

A quick, inexpensive and easy assay to run is an in vitro cell free assay. In the present invention, it only is necessary that a cell free system include sufficient components that one or more reactions leading to glycosaminoglycan production be operable.

3. In cyto Assays

The present invention also contemplates the screening of compounds for their ability to modulate glycosaminoglycan metabolism in cells. Various cell lines can be utilized for such screening assays, including cells specifically engineered for this purpose. Depending on the assay, culture may be required. The cell is examined using any of a number of different assays for glycosaminoglycan metabolism.

4. In vivo Assays

In vivo assays involve the use of various animal models. Due to their size, ease of handling, and information on their physiology and genetic make-up, mice are a preferred embodiment. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to a cell (e.g., growth, tumorigenicity, survival), or instead a broader indication such as behavior, anemia, immune response, etc.).

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Chemical Modifications of Pep-1

Pep-1 was subject to chemical modifications to obtain a more high-throughput and cost-effective derivative. The present inventors discovered derivatives that had several desirable properties that significantly enhance their and clinical applicability as well. For example, the derivatives were highly water soluble, did not require additional solvents for dissolution, higher affinity for the glycosaminoglycan substrate (e.g., HA), and were more effective biologically.

Synthesis of the Pep-1 Dimer. The Pep-1 dimer was synthesized by adding two moles of Pep-1 per mole of succinic acid in 0.1 NHCl, in the presence of 10-fold molar excess of 1-ethyl-3-(3-dimethylaminopropyl)carbodiimide relative to succinic acid and was subsequently purified by size-exclusion column chromatography.

Properties of the Pep-1 Dimer. The Pep-1 dimer was soluble in the absence of added solvents such as DMSO and exhibited significant biological activities to prevent HA-mediated leukocyte adhesion. As the Pep-1 dimer formulation has a high solubility it is an ideal choice for local administration in therapeutic applications.

Synthesis of the Pep-1 Tetramer. The Pep-1 tetramer, also referred to as the PEG-conjugate of Pep-1 was prepared by adding 10 to 20-fold molar excess amounts of Pep-1 to bis(polyoxyethylene bis[imidazolyl carbonyl]) along with triethylamine. The reaction is allowed to proceed for 5–7 days at 37° C. Afterwards, the reagent is dried under air and resuspended in PBS. Free peptide is removed by dialysis against PBS. Alternatively, the reagent can be directly dialyzed in Spectra/Por® tubing without drying.

Properties of the Pep-1 Tetramer. This Pep-1 tetramer obtained by PEG-conjugated Pep-1 remained soluble in the absence of added solvents (e.g., DMSO) and exhibited significant biological activities to prevent HA-mediated leukocyte adhesion. The PEG-conjugated Pep-1 was also found to be at least 10-fold more active than Pep-1 in its capacity to inhibit in vitro adhesion of B16F10 melanoma cells to the HA-coated substrates.

The inventors contemplate that the PEG-conjugated Pep-1 will be relatively resistant to renal filtration and proteolytic digestion as compared to the original Pep-1. Thus, it is contemplated that PEG-conjugated Pep-1 will be an ideal formulation for systemic administration.

Example 2

Comparison of Pep-1 and Derivatives

Figure 3:
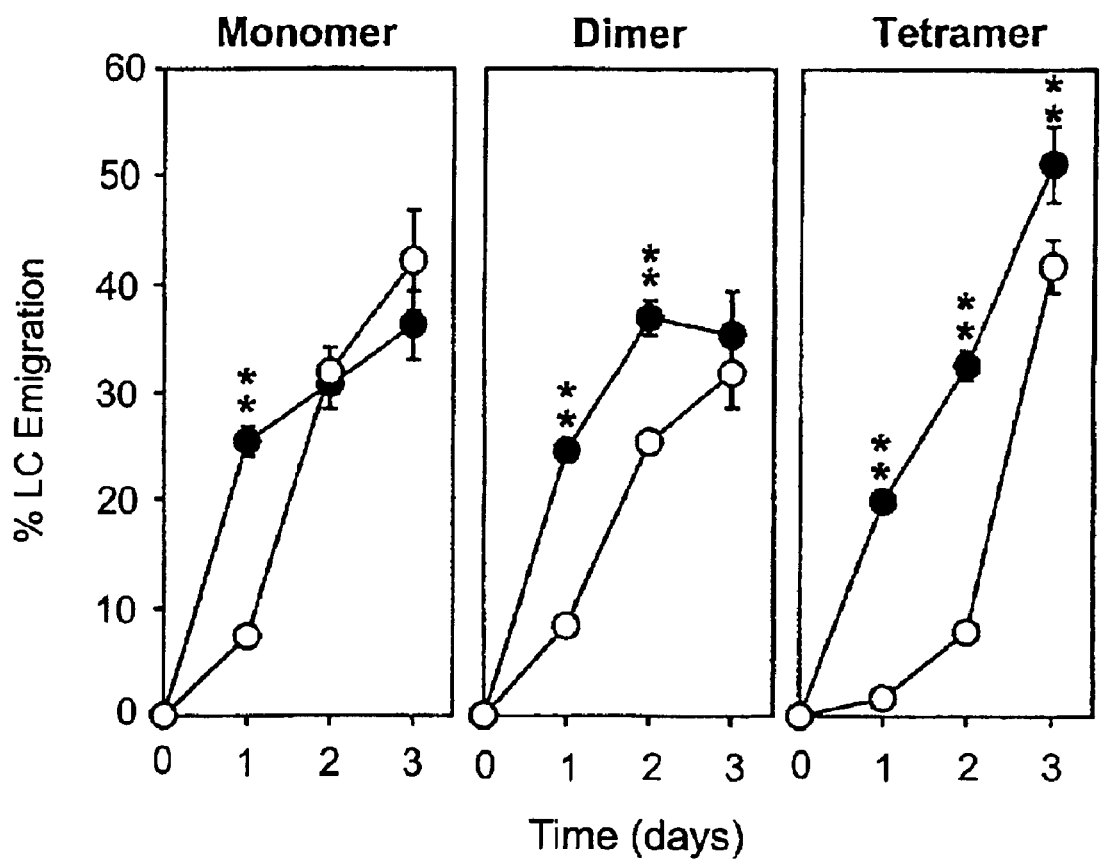
FIG. 3. Impact of multimeric Pep-1 derivatives on hapten-induced LC migration. BALB/c mice received two local injections of the indicated Pep-1 derivatives in the right ear (closed circles) and the indicated RP derivatives in the left ear 24 and 3 hours before topical application of 0.5% DNFB on both ears. All the peptides were administered at the identical dose in terms of the molarity (24 mmol/injection) of the 16-mer Pep-1 peptide sequence, i.e., 40 μg/injection/ear for monomeric Pep-1 and RP, 41 μg/injection/ear for dimeric Pep-1 and RP, or 160 μg/injection/ear for PEG-conjugated tetrameric Pep-1 and RP. Ear skin samples were harvested at the indicated time points after DNFB painting and examined for surface densities of IA$^+$ LC. Data shown are the means+/−s.e.m.(n=3) of % LC emigration as calculated by dividing from the formula: [(LC number before DNFB application−LC number after DNFB application)/LC number before DNFB application]×100. Asterisks indicate statistically significant differences between the Pep-1 and the RP panels (**p<0.01 by two-tailed Student's t-test).

Pep-1 and its dimeric and tetrameric derivatives were compared for their in vivo activities to prevent hapten-triggered LC emigration from the epidermis. Two local injections of the original monomeric Pep-1 before DNFB application inhibited LC emigration almost completely when tested at 24 hr after DNFB painting. However, LC began to migrate from Pep-1-injected skin sites at later time points (48 and 72 hrs after DNFB application) with the kinetics comparable to those observed in the control group receiving random peptide (RP) injections (FIG. 3). By marked contrast, the dimeric form at the same concentration in terms of the molarity of the Pep-1 sequence inhibited LC migration significantly at 24 and 48 hrs after DNFB application. Moreover, the tetrameric form prevented LC migration almost completely at 24 and 48 hr and significant ($P<0.01$) inhibition was still observed even at 72 hr.

Figure 2:
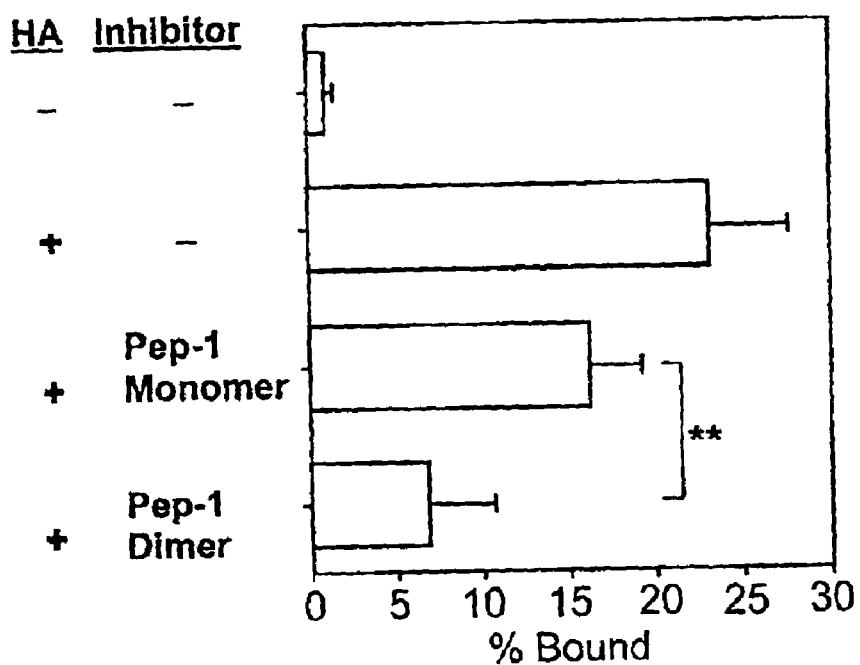
FIGS. 2A–B. Improved biological activities of Pep-1 dimer and tetramer. Three different Pep-1 derivatives were compared for their biological activities at the same concentration in terms of the molarity (150 μM) of the 16-mer Pep-1 peptide sequence. HA-coated plates (0.1 μg/ml) were pre-treated for 3 hr with Pep-1 (249 μg/ml), Pep-1 dimer (258 μg/ml) (FIG. 2A), or Pep-1 tetramer (998 μg/ml) (FIG. 2B). $^{35}$S-labeled B16-F10 melanoma cells were then examined for their binding to these plates. Data shown are the means+/−S.D. of % binding from quadruplicate samples. Asterisks indicate statistically significant differences (**p<0.01 by two-tailed Student's t-test).
Figure 2:
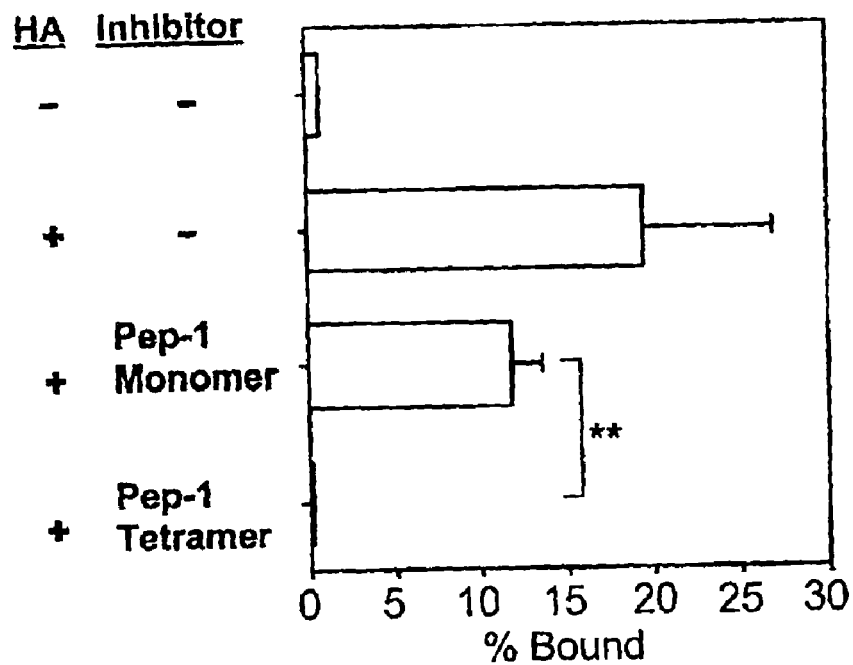

In other studies that measured inhibition of HA-mediated cell adhesion, monomeric Pep-1, at a suboptimal concentration (150 $\mu$M), showed only modest inhibition (see FIGS. 2A–B). By contrast, dimeric Pep-1 and tetrameric Pep-1 at the same concentration in terms of the molarity of the Pep-1 peptide sequence produced significantly ($P<0.01$) improved inhibition (FIG. 2A), with almost complete inhibition achieved with the tetrameric form (FIG. 2B). Thus, the multimeric derivatives of Pep-1 demonstrate an enhanced improvement of in vivo pharmacological activities of Pep-1.

Example 3

Role in Preventing Metastasis

Surface expression of particular CD44 isoforms has been observed in many cancers and CD44 inhibitors have been showed to inhibit cancer metastasis in many animal tumor models. Thus, the present inventors determined the potential of Pep-1, an inhibitor of HA function, to prevent tumor metastasis using a fully established model of experimentally induced lung metastasis of in vivo infused B16-F10 melanoma cells[76].

Figure 4:
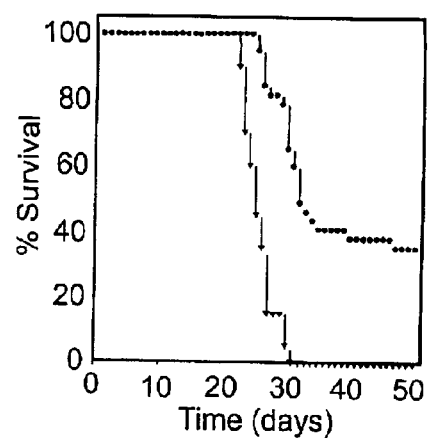
FIGS. 4A–C. Impact of Pep-1 on lung metastasis of melanoma.
Figure 4:
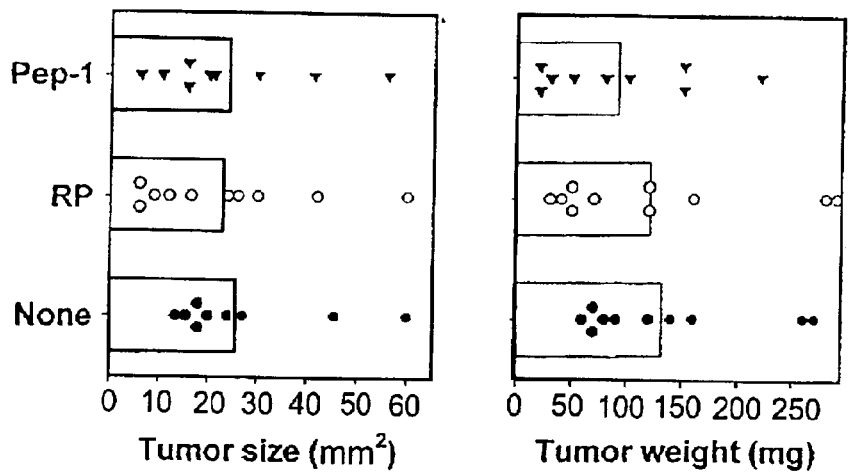
Figure 4:
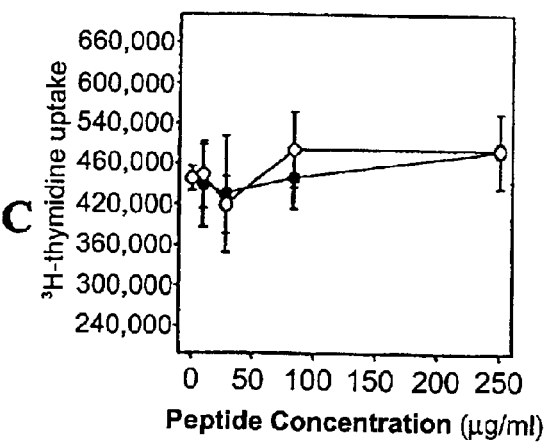

In the model, melanoma cells and Pep-1 (or random peptide control or PBS alone) were injected together intravenously into syngeneic C57BL/6 mice and lung metastasis was examined macroscopically and by following-up the survival of mice. As reported by other investigators, multiple macroscopic satellite regions were observed in the lung in 10 days after tumor inoculation. Simultaneous i.v. injection of Pep-1 (the original monomeric form) together with B16-F10 melanoma cells reduced the extent of lung metastasis significantly as compared to the RP control panel. Moreover, Pep-1 prolonged the survival of recipient animals significantly (FIG. 4A). On the other hand, Pep-1 had no apparent effects on the in vitro growth of B16-F10 melanoma cells or on local growth in animals following s.c. inoculation (FIG. 4B and FIG. 4C). Finally, the B16-F10 melanoma cells showed marked adhesion to the HA-coated plates, and this adhesive interaction was blocked efficiently by Pep-1, especially in the tetrameric form (FIGS. 2A–B), illustrating a mechanism by which Pep-1 interferes with HA-mediated adhesion and trafficking of melanoma cells. In all four independent experiments, Pep-1 always prevented melanoma metastasis and prolonged the survival of animals significantly. The inventors have therefore demonstrated that lung metastasis of B16-F10 mouse melanoma cell line can be inhibited by simultaneous administration of Pep-1. These results have revealed an additional pharmacological activity of Pep-1 to specifically prevent tumor metastasis. The inventors will also examine the prophylactic and therapeutic potentials of multimeric Pep-1 formulations and other chemically modified Pep-1 derivatives using this animal model of melanoma metastasis.

Example 4

Impact of Pep-1 on DC-T Cell Interaction

During antigen-specific interaction DC delivers activation signals to T cells, leading to differentiation and clonal expansion of antigen-reactive T cells. At the same time, T cells deliver signals back to DC, leading to "terminal maturation" of DC[80]. To test the potential impact of Pep-1 on this bi-directional DC-T cell interaction, the present inventors employed a fully characterized in vitro experimental system in which XS52 DC are cultured with a KLH-reactive CD4+ Th1 clone HDK-1 in the presence of antigen (KLH)[81-85].

Figure 7:
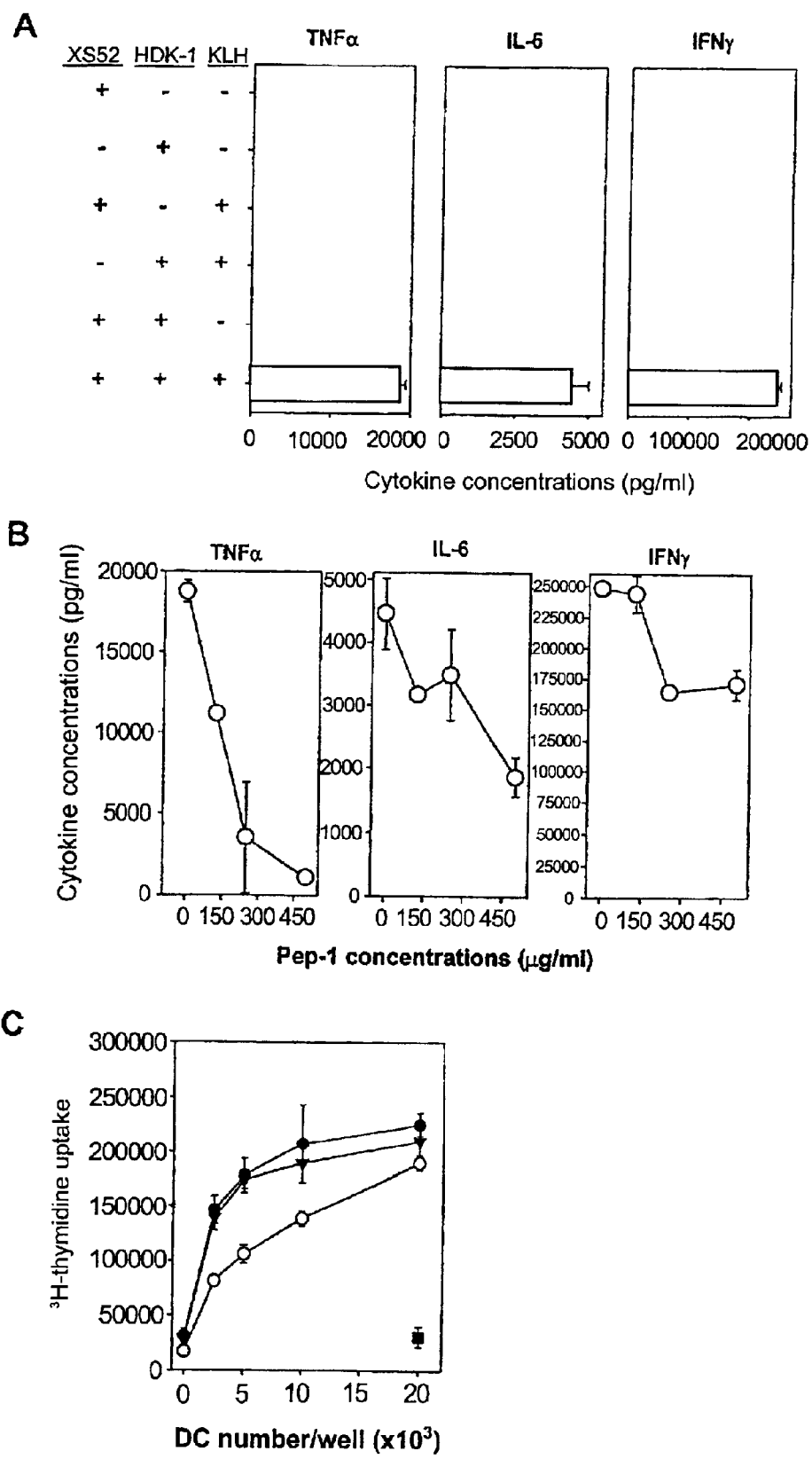
FIGS. 7A–C. Impact of tetrameric LIP on cytokine production during antigen presentation.

It was found, that Pep-1 inhibited, in a dose-dependent fashion, the secretion of TNFα (by both XS52 and HDK-1 cells), IL-6 (by both cell types) and interferon-γ (by HDK-1 cells), with almost complete inhibition achieved at 500 μg/ml (FIG. 7B). These results document another previously unrecognized function of HA in antigen presentation, namely, high molecular weight HA and/or its degradation products provide an essential stimulatory signal during antigen-specific DC-T cell interaction. Importantly, the present invention also revealed another pharmacological activity of Pep-1, which is suppression of antigen presentation. Pep-1 also inhibited the activation of immunologically naive CD4+ T cells by splenic dendritic cells (FIG. 7C).

Example 5

Degradation Products of HA

There has been accumulating evidence in the art, to support the new concept that degradation products of HA (i.e., HA fragments), just like fragments of other extracellular matrix components (e.g., collagens and fibronectin), act as pro-inflammatory mediators. The present inventors have demonstrated that HA fragments trigger cytokine production from DC, e.g., IL-6 and TNF alpha production by the XS52 DC line. In addition, the inventors have demonstrated that the glycosaminoglycan peptide-inhibitors of the invention, including Pep-1 and its derivatives, significantly block the production of both cytokines by XS52 cells following stimulation with HA fragments.

Figure 5:
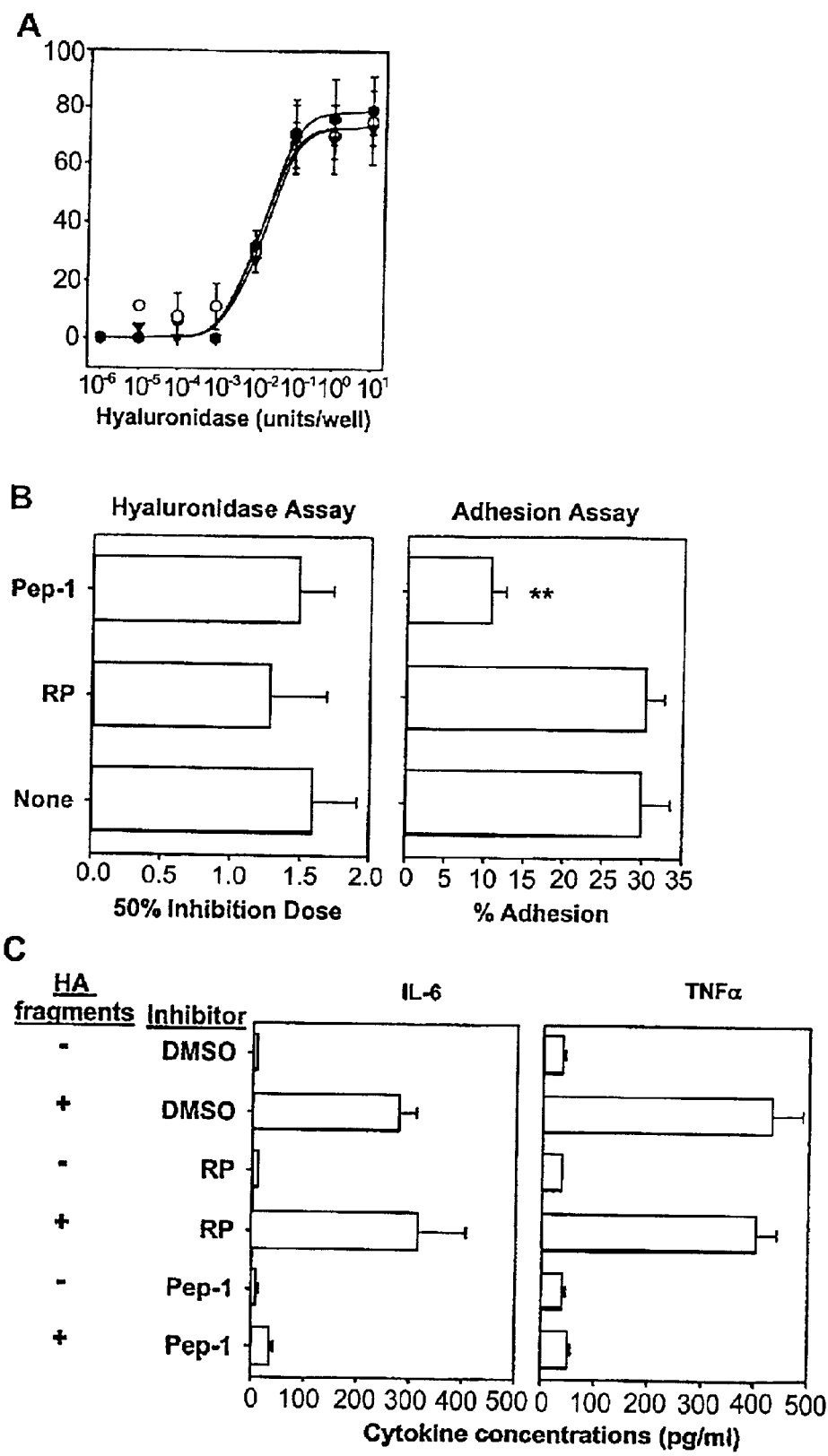
FIGS. 5A–C. Impact of Pep-1 on HA degradation products.

To test the impact of Pep-1 on HA degradation, the present inventors developed a 96 well-based assay in which biotinylated HA was immobilized onto the plates and treated with HAase. The amounts of HA that remained attached to the wells was then determined by addition of streptavidin-conjugated alkaline phosphatase (FIG. 5A). Pep-1 failed to affect the degradation of HA substrates in this assay, while Pep-1 at the same concentration blocked BW5147 cell adhesion to the same HA substrate prepared in parallel (FIG. 5B). This indicates that Pep-1 is not merely acting as a non-specific masking reagent for HA.

To test the potential impact of Pep-1 on pro-inflammatory activities of HA fragments, low molecular weight HA fragments were prepared by sonication and enzymatic digestion of HA and the resulting fragments were added to the immature DC line XS52. The inventors HA fragment preparation triggered the secretion of IL-6 and TNFα by XS52 cells (FIG. 5C). Importantly, Pep-1, but not RP, inhibited the secretion of both cytokines almost completely. These results have unveiled yet another pharmacological activity of Pep-1, that comprises neutralizing the DC-stimulatory potential of HA fragments.

Figure 6:
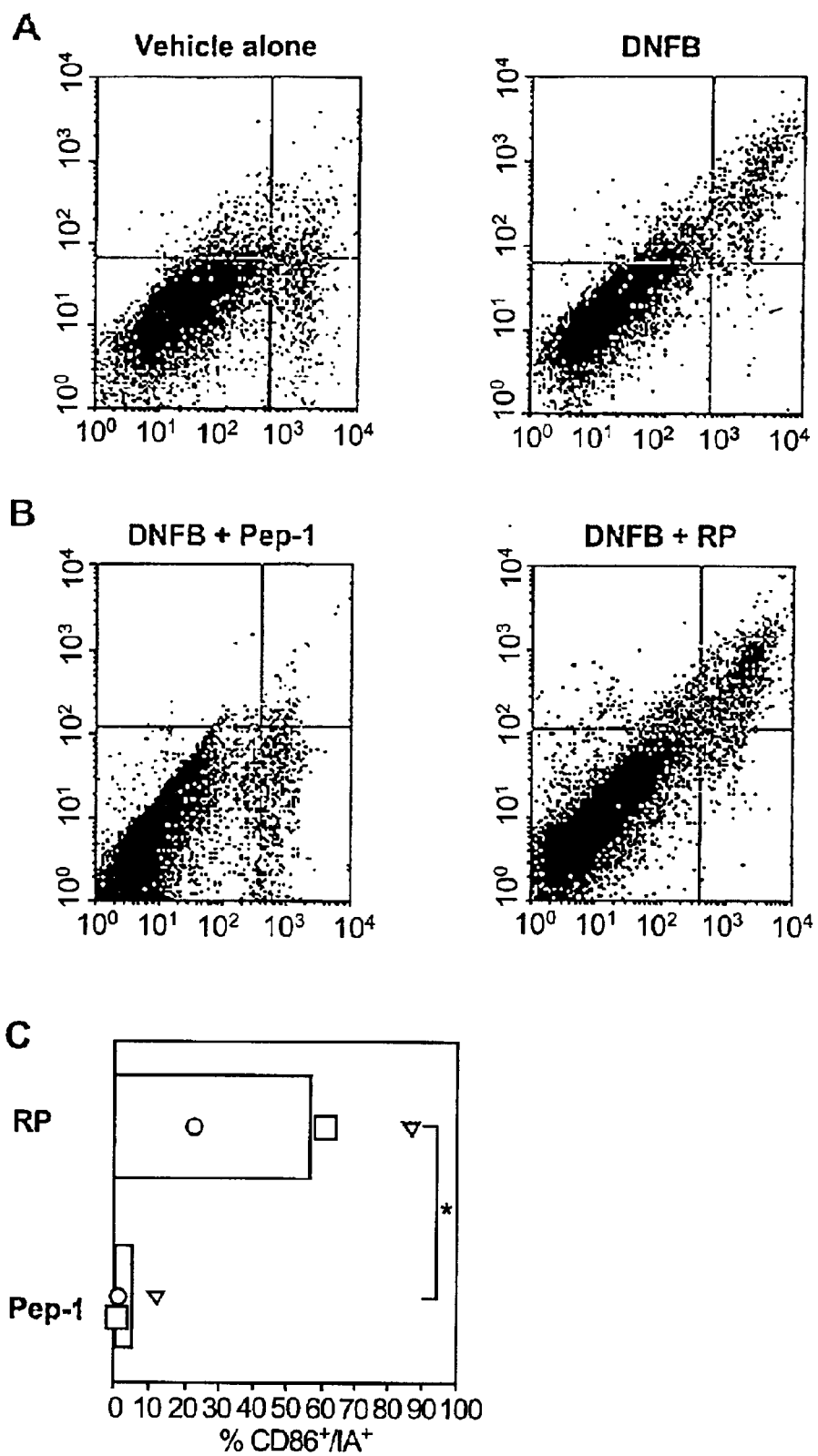
FIGS. 6A–C. Impact of Pep-1 on hapten-induced LC maturation.

A critical question concerns the physiological significance of the above finding. Topical application of haptens is known to trigger not only LC migration from the epidermis, but also their maturation. Thus, the impact of locally injected Pep-1 on DNFB-induced LC maturation was tested in situ by testing surface expression of CD86 by IA+ epidermal cells (i.e., LC). LC isolated from vehicle-treated skin expressed CD86 at minimal levels, whereas LC from DNFB-treated skin showed significantly elevated CD86 expression (FIG. 6A). Importantly, two local injections of Pep-1, but not RP, prevented this DNFB-induced LC maturation in three independent experiments (FIGS. 6B and 6C). Not only do these results support the inventors hypothesis that Pep-1 can be used to prevent DC maturation in vivo, they also imply that HA degradation must take place in the epidermal compartment in response to hapten application.

Example 6

HA Expression and Metabolism

The inventors observations, described in Example above, indicate the potential of keratinocytes and DC to synthesize and degrade HA either spontaneously or upon activation. Three HA synthases (I, II, and III) and two HAases (I and III) have been cloned in mice, and the present inventors have identified a mouse homologue of human HAase II from the EST database. In RT-PCR experiments, the present inventors detected constitutive mRNA expression of HA synthases-2 and-3 and HAases-1, 2, and 3 in mouse skin (see Table 2). PCR signals for the same enzymes were detected in the Pam 212 keratinocyte, XS52 DC, XS106 DC, and NS46 fibroblast lines.

The data in Table 2 depict the RT-PCR results, where total RNA was isolated from BALB/c mouse skin or the indicated cell lines, reverse-transcribed and examined for expression of the indicated mRNA by PCR using the following primer pairs:

```
5'-TATCCAACCGGCCATTCAATCACTG-3'  (SEQ ID NO:3) and

5'-ATACCCCGCTTGTCACACCACTTG-3'  (SEQ ID NO:4) for HAase-1;

5'-CATCTTCACTGGCCGACCCTTTGT-3'  (SEQ ID NO:5) and

5'-TCGCCACCCCAGCCCAGATAGC-3'    (SEQ ID NO:6) for HAase-2; and

5'-CCTAGGCCTAATGATGGTG-3'       (SEQ ID NO:7) and

5'-GCTAGTATGGGCTTTGTGG-3'       (SEQ ID NO:8) for HAase-3;

5'-CTACGGGCGCTGTCGGTGAAGGT-3'   (SEQ ID NO:9) and

5'-CGGGGACATAGTTAGCAGCCAGTT-3'  (SEQ ID NO:10) for HA synthase-1;

5'-TGGAACACCGGAAAATGAAGAAG-3'   (SEQ ID NO:11) and

5'-GACCGAGCCGTGTATTTAGTTGC-3'   (SEQ ID NO:12) for HA synthase 2; and

5'-CCATGAGGCGGGTGAAGGAGAG-3'    (SEQ ID NO:13) and

5'-ATGCGGCCACGGTAGAAAAGTTGT-3'  (SEQ ID NO:14) for HA synthase-3';
```

No PCR signals were detected for HA synthase-1. The data shown in Table 2 are PCR products after 35 cycles of amplification visualized with ethidium bromide.

Detection of mRNA for hyaluronidases and for hyaluronan synthases in keratinocytes demonstrate that several enzymes involved in HA metabolism are expressed at least at the mRNA levels by the Pam 212 keratinocyte line and in mouse skin. This indicates that keratinocytes (and other cell types in the skin) can potentially produce HA fragments in response to environmental stimuli. These observations also validate the topical application of Pep-1 to neutralize the pro-inflammatory activities of locally produced HA fragments.

TABLE 2 mRNA Expression of HA Synthases and HAases by Diverse Cell Types in Skin

|  | Skin | Pam212 KC | XS52 DC | XS106 DC | NS47 FB | No Template |
|---|---|---|---|---|---|---|
| HAse 1 | + | ++ | ++ | ++ | ++ | − |
| HAse 2 | + | ++ | ++ | ++ | ++ | − |
| HAse 3 | ++ | ++ | ++ | ++ | ++ | − |
| HA Synthase 2 | + | ++ | + | ++ | + | − |
| HA Synthase 3 | + | + | ++ | ++ | + | − |
| β-Actin | ++ | ++ | ++ | ++ | ++ | − |

++ Indicates strong expression
+ Indicates expression
− Indicates no expression

Figure 8:
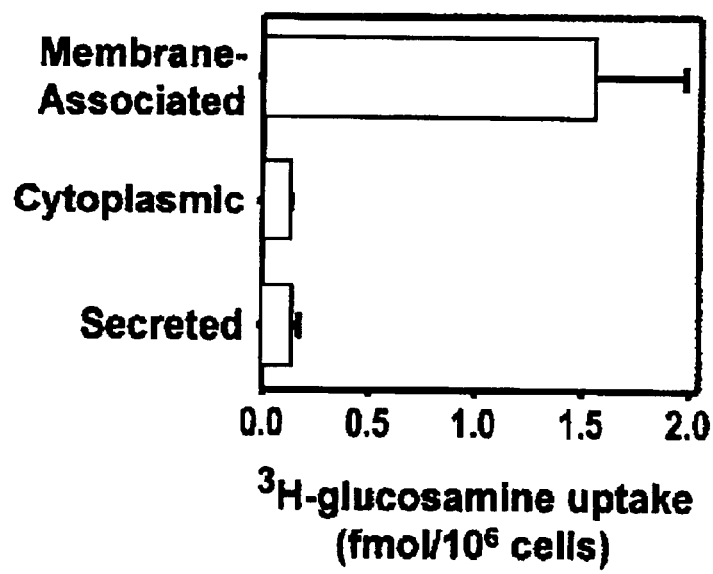
FIGS. 8B–D. Synthesis and surface expression of HA by DC. (B) XS106 DC were labeled with $^3$H-glucosamine and then examined for the incorporation of hyaluronidase-sensitive radioactivities (means+/−s.e.m.; n=5) into the indicated subcellular fractions. (C) XS106 DC were incubated with biotinylated Pep-1 or RP and then with PE-conjugated streptavidin (filed histograms) (Mummert et al. J. Exp. Med. 192:769–779, 2000) or bovine testis hyaluronidase. Baseline staining levels with PE-streptavidin alone are shown with open histograms. (D) The indicated DC preparations were examined for binding of biotinylated Pep-1 (filled) and RP (open). Peptide binding to splenic DC and bone marrow-DC was examined within the CD11c$^+$ populations. Binding of biotinylated Pep-1 was significantly diminished after hyaluronidase pretreatment in each DC preparation (data not shown).
Figure 8:
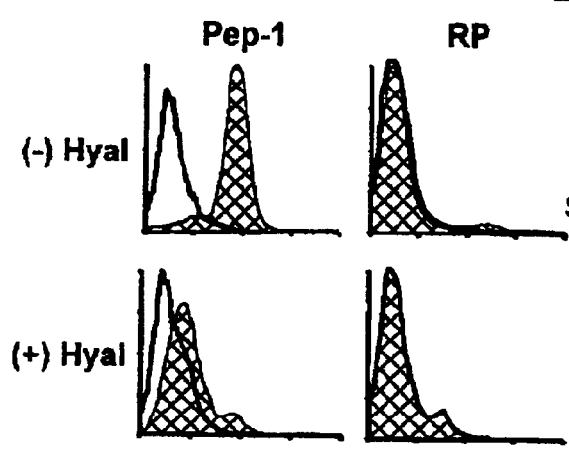
Figure 8:
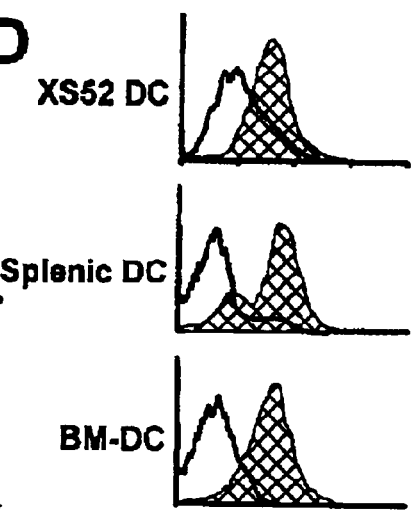

Metabolic labeling of XS106 DC with $^3$H-glucosamine revealed that hyaluronidase is incorporated most predominantly into membrane (FIG. 8B). Moreover, Pep-1 in a biotinylated form bound to the surfaces of XS106 DC (FIG. 8C). A 12-mer control peptide (SATPASAPYPLA), termed "random peptide" (RP), showed no significant binding, and Pep-1 binding was abolished almost completely by hyaluronidase pretreatment of DC (FIG. 8C). Pep-1 also bound to all other tested DC preparations, including XS52 DC, splenic DC, and bone marrow-derived DC (FIG. 8D). In double-staining experiments, in which XS106 DC were double-stained with biotinylated Pep-1 or RP followed by FITC-conjugated streptavidin and with PE-conjugated anti-CD44 mAb, biotinylated Pep-1 showed diffuse and uniform binding to the cell bodies, whereas phycoerythrin (PE)-conjugated anti-CD44 mAb exhibited somewhat distinct binding profiles.

Example 7

Function of HA in T Cell Communication and Proliferation

Figure 9:
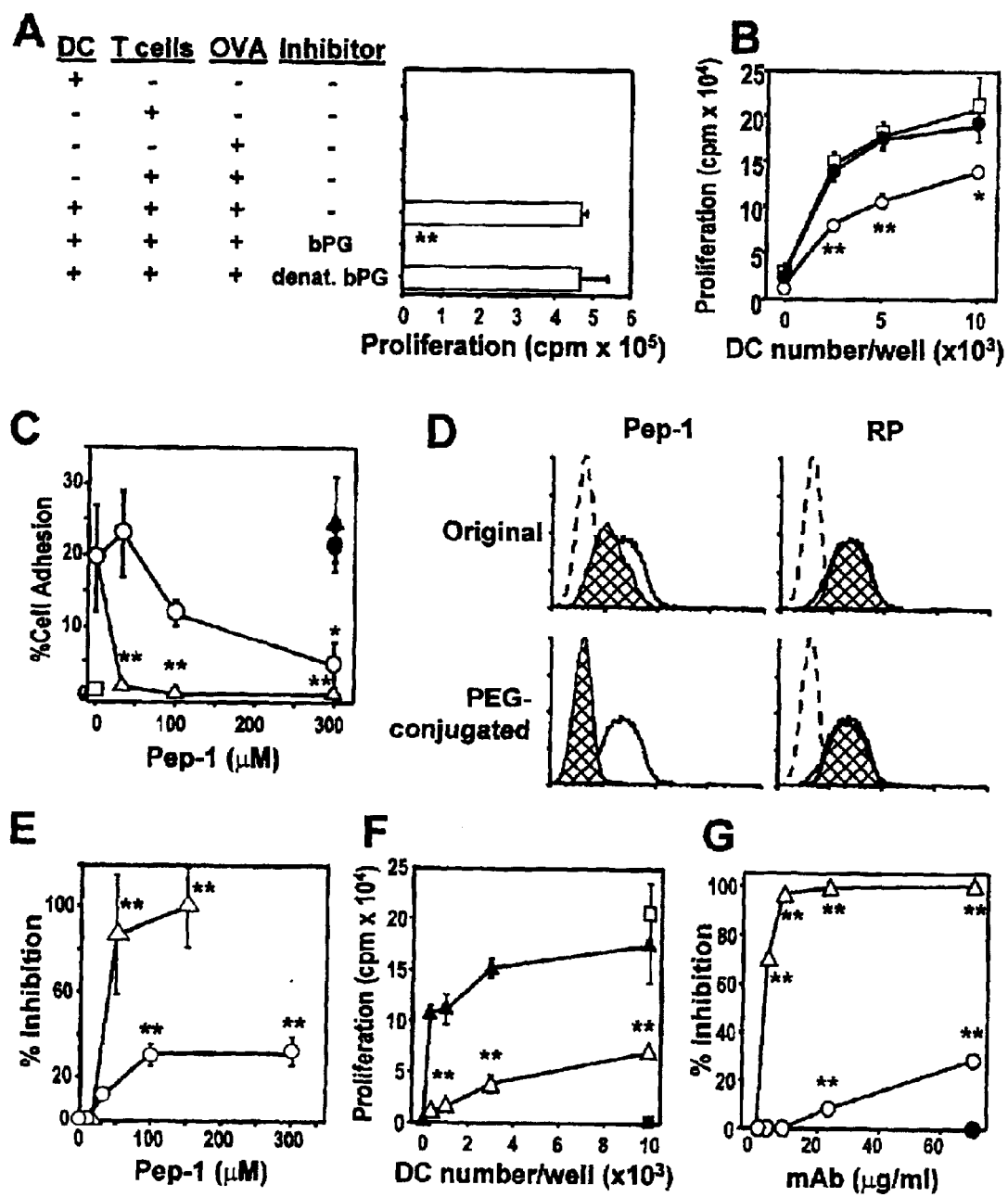
FIGS. 9A–G. DC-associated HA and DC-dependent T cell proliferation. (A) DO11.10 T cells were cultured with y-irradiated splenic DC and/or OVA$_{323-339}$ (2 μg/ml) in the presence of intact bPG (250 μg/ml), heat-denatured bPG, or PBS alone. Data shown are the means+/−s.d. (n=3) of $^3$H-thymidine uptake. (B) DO11.10 T cells were cultured with the indicated numbers of splenic DC and OVA$_{323-339}$ in the presence of Pep-1 (300 μM) (open circles), RP (closed circles), or PBS alone (squares). (C) Pep-1 (open circles) or PEG-conjugated Pep-1 (open triangles) were compared at the indicated concentrations (in terms of the molarity of the 12-mer Pep-1 sequence) for their abilities to inhibit the adhesion of $^{35}$S-labeled B16 melanoma cells onto the HA-coated plates (Mummert et al. J. Exp. Med. 192:769–779, 2000). The % cell adhesion to non-coated plates is indicated with an open square. RP (closed circle) and PEG-conjugated RP (closed triangle) served as controls. (D) The indicated inhibitors (300 μM) were compared for their abilities to inhibit the binding of FITC-labeled HA to BW5147 cell surfaces (filled histograms) (Mummert et al. J. Exp. Med. 192:769–779, 2000). Maximal binding in the absence of added inhibitors and autofluorescence in the absence of FITC-HA are indicated with solid lines and broken lines, respectively. (E) Pep-1 (open circles) or PEG-conjugated Pep-1 (open triangles) were compared at the indicated concentrations for their abilities to inhibit DO11.10 T cell proliferation triggered by splenic DC. (F) DO11.10 T cells were cultured with the indicated numbers of bone marrow-derived DC and OVA$_{323-339}$ in the presence of PEG-Pep-1 (60 μM) (open triangles), PEG-RP (closed triangles), or PBS alone (open square). The baseline response in the absence of OVA$_{323-339}$ is indicated with a closed square. (G) DO11.10 T cells were cultured with splenic DC and OVA$_{323-339}$ in the presence of anti-CD44 mAb (KM81) (open circles) or isotype-matched control IgG (closed circle) at the indicated concentrations. The same anti-CD44 mAb preparation was examined in parallel for its ability to inhibit the adhesion of $^{35}$S-labeled T cells onto the HA-coated plates (open triangles). All the data in this figure are representative of at least two independent experiments. Statistically significant differences assessed by a two-tailed Student's t-test for comparing two groups or by analysis of variance (ANOVA) followed by LSD for multiple comparisons are indicated by asterisks (*P<0.05, **P<0.01).

CD4$^+$ T cells purified from DO11.10 mice (BALB/c background) express the transgenic T cell receptor α- and β-chains specific for ovalbumin (OVA) peptide 323–339, providing an unique opportunity to study the potential contribution of HA being expressed on DC to their intrinsic capacity to activate naive T cells. DO11.10 T cells showed robust $^3$H-thymidine uptake when stimulated by splenic DC (isolated from BALB/c mice) in the presence of OVA$_{323-339}$ (FIG. 9A). By contrast, no significant proliferation was observed in the absence of DC or antigen, indicating DC-dependency and antigen-specificity.

Bovine proteoglycan (bPG), which is known to bind to and inhibit the function of HA specifically, abolished the proliferative responses of DO11.10 T cells completely, whereas it showed no inhibitory potential after heat inactivation (FIG. 9A). DC-dependent, antigen-specific T cell proliferation was also inhibited by Pep-1 (FIG. 9B). Pep-1 molecules were conjugated to a tetravalent polyethylene glycol (PEG) derivative by incubating a 40-fold molar excess of Pep-1 or RP with bis(polyethylene bis[imidazolyl carbonyl]) in DMSO containing 0.5% triethylamine for 7 days. Reactions were terminated by extensive dialysis against dH$_2$O or PBS and the density of substitution was estimated by the BCA assay (to determine peptide content) and dry weight analysis. The resulting preparations, which showed an estimated molecular ratio of Pep-1/PEG of 2.3–2.9 (data not shown), were significantly more potent than the original Pep-1 preparations in blocking both cell adhesion to HA-coated plates (FIG. 2C) and cellular binding of soluble HA (FIG. 9D). The PEG-conjugated Pep-1 formulation inhibited splenic DC-dependent DO11.10 T cell proliferation almost completely (80–100%) even at lower concentrations (50–150 µM in terms of the molarity of the 12-mer Pep-1 sequence) (FIG. 9E). PEG-Pep-1, but not PEG-RP, also efficiently inhibited DO11.10 T cell proliferation triggered by bone marrow-derived DC (FIG. 9F). Anti-CD44 mAb (KM81) affected DC-induced T cell proliferation only partially even at the concentration 10 times higher than that required to completely block T cell adhesion to HA-coated plates (FIG. 9G). This may suggest that CD44 is not the only relevant receptor for DC-associated HA. Alternatively, T cells may employ different CD44 isoforms to recognize HA moieties expressed on DC surfaces versus HA molecules immobilized on culture plates. Nevertheless, the data indicate that blockade of DC-associated HA with each tested inhibitor markedly diminishes the intrinsic ability of DC to trigger T cell proliferation.

Figure 10:
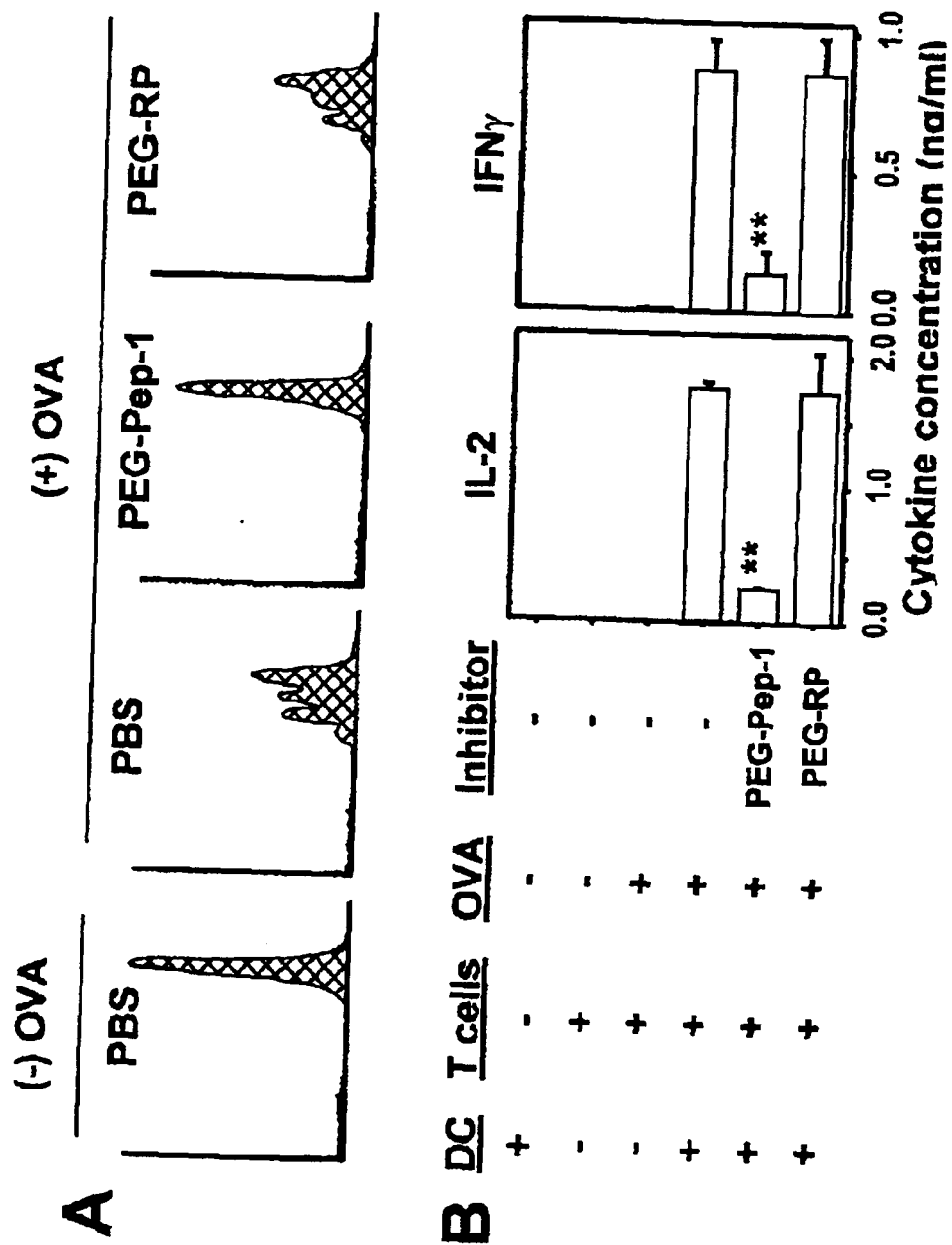
FIGS. 10A–B. DC-associated HA mediates DC-T cell communication during antigen presentation. (A) CSFE-labeled DO11.10 T cells were cultured with splenic DC and/or $OVA_{323-339}$ in the presence of PEG-Pep-1 (60 $\mu$M), PEG-RP, or PBS alone. Data shown are the CSFE fluorescence profiles within the PI-negative populations. (B) DO11.10 T cells were cultured with splenic DC and/or $OVA_{323-339}$ in the presence of PEG-Pep-1 (60 $\mu$M), PEG-RP, or PBS alone. Culture supernatants (24 hr) were then tested for the indicated cytokines by ELISA. All data shown in this figure are representative of two independent experiments.

To test whether PEG-Pep 1 inhibited T cell proliferation by causing cell death, the Inventors examined T cell proliferation by using a fluorescence dye 5,6-carboxy-succinimidyl-fluorescein-ester (CSFE). When stimulated by DC in the presence of OVA$_{323-339}$, CSFE-labeled DO11.10 T cells showed marked reduction in the fluorescence intensities, reflecting their progressive mitosis (FIG. 10A). By contrast, no significant mitotic activity was observed in the absence of antigen. Consistent with our observations in $^3$H-thymidine uptake assays, T cell mitosis was prevented completely by PEG-Pep-1, but not PEG-RP. It should be noted that the Inventors examined CSFE profiles within the propidium iodide (PI)-negative populations. Thus, PEG-Pep-1 inhibits the growth of T cells without affecting their viability. PEG-Pep-1 showed no significant effect on the viability of DC, as measured by PI uptake within the CD11c$^+$ populations. To test the possibility that PEG-Pep 1 may inpair the overall ability of DC to deliver T cell activation signals, the Inventors measured cytokine release from T cells. DO11.10 T cells secreted significant amounts of IL-2 and interferon-γ (IFNγ) only when stimulated by DC in the presence of antigen (FIG. 10B). Production of both cytokines was inhibited efficiently by PEG-Pep-1, but not by PEG-RP, suggesting that antigen-specific DC-T cell communication is broadly impaired. To test whether PEG Pep 1 might physically block the contact between DC and T cells during antigen presentation, the Inventors examined DC-T cell cluster formation. DO11.10 T cells were cultured with bone marrow-derived DC and/or OVA$_{323-339}$ in the presence of PEG-Pep-1 (60 µM), PEG-RP, or PBS alone. DO11.10 T cells formed relatively large clusters with DC after 16 hr co-culturing in the presence of OVA$_{323-339}$ By contrast, only a few clusters were observed in the absence of antigen. This antigen-specific DC-T cell cluster formation was blocked almost completely by PEG-Pep-1, but not by PEG-RP. Thus, HA molecules expressed on DC facilitate the establishment of physical contact and the subsequent intercellular communication between DC and T cells during antigen presentation.

Figure 11:
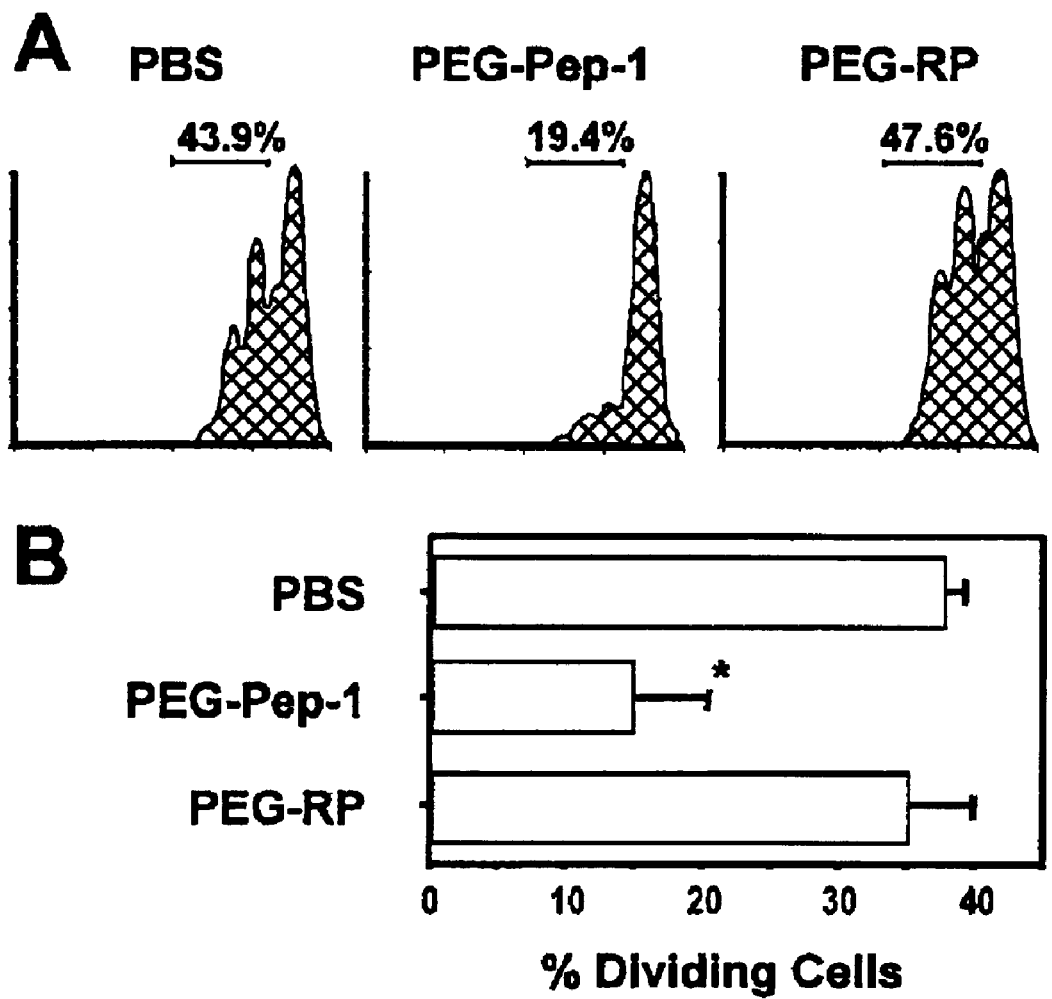
FIG. 11. A-B. In vivo inhibition of DC-dependent T cell activation by PEG-Pep-1. (A and B) CSFE-labeled DO11.10 T cells ($10^6$ cells/animal) and $OVA_{323-339}$-pulsed bone marrow-DC ($3\times10^5$ cells/animal) were injected intraperitoneally into BALB/c mice. These animals also received simultaneous intraperitoneal injection of PEG-Pep-1 (20 $\mu$g/animal), PEG-RP, or PBS alone. Data shown are representative CSFE fluorescence profiles and % dividing cells within the PI-negative populations collected from the peritoneal cavity 48 hr later (A) and the means+/−s.e.m. of % dividing cells from triplicate animals (B). Data shown in this figure are representative of two independent animal experiments.

The Inventors developed an in vivo assay for testing homing-independent DC-T cell interaction. This method involves intraperitoneally injecting OVA$_{323-339}$-pulsed DC and CSFE-labeled DO11.10 T cells and examining the CSFE profiles of the cells recovered from the peritoneal cavity. Significant reduction in the fluorescence intensities was detected in those animals receiving antigen-pulsed DC, but not PBS-pulsed DC, validating antigen-specificity of the new assay system. Intraperitoneal administration of PEG-Pep-1, but not PEG-RP, appeared to inhibit the mitosis of DO11.10 T cells (FIG. 11A). In fact, the PEG-Pep-1 treatment panel showed a statistically significant reduction in the % of dividing cells in two independent experiments, as compared to the non-treatment panel and to the second control panel receiving PEG-RP injection (FIG. 11B).

The Inventors have identified a capability of DC to constitutively express mRNAs for various enzymes involved in HA synthesis and degradation, actively synthesize HA, preferentially incorporate newly synthesized HA into membrane fractions, and uniformly express HA on their surfaces. With respect to the function of DC-associated HA, DC-dependent, antigen-specific proliferation of CD4$^+$ T cells was inhibited by two distinct HA inhibitors (bPG and Pep-1). Moreover, the oligomeric Pep-1 formulation blocked almost completely antigen-specific DC-T cell cluster formation, DC-induced cytokine production by T cells, and in vivo DC-T cell interaction. Thus, it is proposed proposed that HA molecules expressed on DC mediate intercellular communication between DC and T cells during antigen presentation.

Example 8

Method of Screening for an Inhibitor of Glycosaminoglycan-Mediated Reactions

Agents, for example other peptides, macromolecules or small molecules, that bind glycosaminoglycans, in particular HA, can be discovered using various screening methods. For example beads or other supports treated linked to HA are pre-incubated with agents of interest. Peptides comprising the general formula $(Z)_nX(Y)_m$, SEQ ID NO:1 or SEQ ID NO:2, multimer peptides comprising the general formula $(Z)_nX(Y)_m$, or peptides of the sequence of SEQ ID. NO:15 which bind HA are labeled with $^{125}$I and tested at 50 µg/ml for the binding to the pre-incubated HA-coated beads. The peptides are radiolabeld at the N-terminus using the Bolton-Hunter reagent and incubated for 2 hours at 4° C. Following incubation, the beads are washed three times and the levels of binding detected, and compared to levels of binding detected in control experiments. Agents that bind HA can be identified because they inhibit the binding of the radiolabeled peptide, and this results in a lower level of binding detected in the experimental compared to the control experiments. Similar assays may be peformed using an unlabeled peptides, wherein the binding of peptides to pre-incubated and experimental samples is detected and measured using a specific antibody against the peptide.

Agents can be further assessed for their ability to inhibit HA-mediated reactions using protocols described in the disclosure.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

---

What is claimed is:

1. An artificial multimer of two to four peptides joined via a linker, wherein each of said peptides consists essentially of the amino acid sequence set forth in SEQ ID NO:1, and wherein said multimer binds hyaluronic acid with a binding affinity $K_a$ of at least $5 \times 10^5$ l/mol.

2. The artificial multimer of two to four peptides of claim 1, wherein said multimer comprises two to four peptides having the same amino acid sequence.

3. The artificial multimer of two to four peptides of claim 1, wherein said multimer comprises two to four peptides having different amino acid sequences.

4. The artificial multimer of two to four peptides of claim 1, wherein said multimer is a dimer.

5. The artificial multimer of two to four peptides of claim 1, wherein said multimer is a tetramer.

6. An artificial multimer of two to four peptides, wherein each of said peptides consists essentially of the amino acid sequence GAXWQFXALTVXGGGS, SEQ ID NO. 18 wherein X is any amino acid and wherein said multimer binds hyaluronic acid with a binding affinity $K_a$ of at least $5 \times 10^5$ l/mol.

7. A pharmaceutical composition comprising:
   (a) an artificial multimer of claim 1; and
   (b) a pharmaceutically acceptable carrier.

8. An artificial multimer of two to four peptides joined via a linker, wherein each of said peptides consists essentially of the amino acid sequence set forth in SEQ ID NO:2, and wherein said multimer binds hyaluronic acid with a binding affinity $K_a$ of at least $5 \times 10^5$ l/mol.

9. The artificial multimer of claim 6, wherein the peptides consist essentially of the amino acid sequence GAHWQFN-LATVRGGGS (SEQ ID NO:15).

* * * * *